United States Patent
Dejongh et al.

(10) Patent No.: US 12,403,329 B2
(45) Date of Patent: Sep. 2, 2025

(54) UPDATING PROTON STOPPING POWER MAPS FOR PROTON RADIATION THERAPY TREATMENT PLANNING

(71) Applicant: ProtonVDA LLC, Naperville, IL (US)

(72) Inventors: Don Frederic Dejongh, Batavia, IL (US); Ethan Alan Dejongh, Aurora, IL (US)

(73) Assignee: ProtonVDA LLC, Naperville, IL (US)

( * ) Notice: Subject to any disclaimer, the term of this patent is extended or adjusted under 35 U.S.C. 154(b) by 166 days.

(21) Appl. No.: 18/485,563

(22) Filed: Oct. 12, 2023

(65) Prior Publication Data

US 2024/0131360 A1    Apr. 25, 2024

Related U.S. Application Data

(60) Provisional application No. 63/415,525, filed on Oct. 12, 2022.

(51) Int. Cl.
*A61N 5/10* (2006.01)
*A61B 6/42* (2024.01)

(52) U.S. Cl.
CPC ........... *A61N 5/1039* (2013.01); *A61N 5/103* (2013.01); *A61B 6/4258* (2013.01); *A61N 2005/1087* (2013.01)

(58) Field of Classification Search
CPC ............ A61N 2005/1087–1088; A61N 5/1039
See application file for complete search history.

(56) References Cited

U.S. PATENT DOCUMENTS

| | | | |
|---|---|---|---|
| 10,179,250 B2 * | 1/2019 | Ruebel | A61B 6/032 |
| 10,369,381 B2 * | 8/2019 | Liu | A61B 34/10 |
| 10,376,717 B2 * | 8/2019 | Bennett | A61N 5/1067 |
| 10,413,751 B2 * | 9/2019 | Dempsey | A61N 5/1049 |
| 10,556,126 B2 * | 2/2020 | Amato | A61N 5/1082 |
| 10,625,097 B2 * | 4/2020 | Reno | A61N 5/1037 |
| 10,918,350 B2 * | 2/2021 | Dejongh | A61B 6/587 |
| 11,033,758 B2 * | 6/2021 | Dempsey | A61N 5/1071 |
| 11,110,298 B2 * | 9/2021 | Joe Anto | A61N 5/1037 |
| 11,116,459 B2 * | 9/2021 | Dejongh | G01T 5/00 |
| 11,351,398 B2 * | 6/2022 | Dempsey | A61N 5/1038 |
| 11,684,328 B2 * | 6/2023 | Dejongh | G01T 1/1603 |
| | | | 600/436 |

(Continued)

Primary Examiner — Colin T. Sakamoto
(74) Attorney, Agent, or Firm — Morrison & Foerster LLP

(57) ABSTRACT

Disclosed herein are systems and methods for proton radiation therapy treatment planning that perform deformable image reconstruction and relative stopping power (RSP) maps updating using individual proton measurement data without requiring use of an entire proton radiography image. The systems and methods are capable of using protons from an arbitrary set of angles and/or positions. The iterative method optimally fits protons, while minimizing deviations from the original or deformed RSP map. The systems and methods use a covariance matrix to account for different uncertainties. Each iteration correctly accounts for in the proton data from measurement uncertainties, optimizing the overall fit of the RSP map to the proton data even though each proton does not fit perfectly due to measurement uncertainties. Different weights for the deviations from the original or deformed RSP map may be assigned to different voxels. The different weights may account for correlations in the deviations between voxels.

20 Claims, 19 Drawing Sheets

(56) References Cited

U.S. PATENT DOCUMENTS

| | | | | |
|---|---|---|---|---|
| 11,717,237 B2* | 8/2023 | DeJongh | | G06T 11/006 |
| | | | | 250/363.04 |
| 11,813,105 B2* | 11/2023 | Dejongh | | A61B 6/588 |
| 11,857,808 B2* | 1/2024 | Packer | | G06T 11/005 |
| 11,908,045 B2* | 2/2024 | Dejongh | | G06T 11/005 |
| 12,017,090 B2* | 6/2024 | Dempsey | | A61N 5/1081 |
| 2016/0059039 A1* | 3/2016 | Liu | | A61B 34/10 |
| | | | | 600/1 |
| 2016/0338654 A1* | 11/2016 | Dejongh | | G01T 1/29 |
| 2017/0197099 A1* | 7/2017 | Ruebel | | A61N 5/1049 |
| 2017/0203124 A1* | 7/2017 | Reno | | A61N 5/1037 |
| 2017/0203125 A1* | 7/2017 | Amato | | A61N 5/1039 |
| 2017/0209714 A1* | 7/2017 | Bennett | | A61N 5/1037 |
| 2017/0209715 A1* | 7/2017 | Ruebel | | A61N 5/1067 |
| 2017/0216632 A1* | 8/2017 | Lee | | A61N 5/1049 |
| 2017/0252577 A1* | 9/2017 | Dempsey | | A61N 5/1071 |
| 2017/0259084 A1* | 9/2017 | Bennett | | A61N 5/1049 |
| 2017/0259085 A1* | 9/2017 | Bennett | | A61B 6/032 |
| 2019/0168028 A1* | 6/2019 | Dempsey | | A61N 5/1067 |
| 2019/0200946 A1* | 7/2019 | Dejongh | | A61B 6/032 |
| 2020/0001115 A1* | 1/2020 | Dempsey | | A61N 5/1039 |
| 2020/0179722 A1* | 6/2020 | Packer | | A61N 5/1037 |
| 2020/0261743 A1* | 8/2020 | Joe Anto | | A61N 5/1037 |
| 2021/0077830 A1* | 3/2021 | Bennett | | A61B 6/037 |
| 2021/0204896 A1* | 7/2021 | Dejongh | | A61B 6/547 |
| 2021/0236072 A1* | 8/2021 | Dejongh | | A61B 6/4216 |
| 2022/0054096 A1* | 2/2022 | DeJongh | | G01T 1/2985 |
| 2022/0101572 A1* | 3/2022 | Dejongh | | G06T 11/006 |
| 2022/0305289 A1* | 9/2022 | Dempsey | | A61N 5/1071 |
| 2024/0123257 A1* | 4/2024 | Packer | | G06T 7/149 |

* cited by examiner

MRI

MRI

CT

UPDATING PROTON STOPPING POWER MAPS FOR PROTON RADIATION THERAPY TREATMENT PLANNING

CROSS REFERENCE TO RELATED APPLICATIONS

This application claims the benefit under 35 USC 119 (e) of U.S. Provisional Patent Application No. 63/415,525, filed Oct. 12, 2022, the contents of which are incorporated herein by reference its entirely for all purpose.

FIELD

This disclosure relates to updating proton stopping power maps for proton radiation therapy treatment planning.

BACKGROUND OF THE INVENTION

In radiation therapy, protons provide a superior dose distribution compared to x-rays. This is because protons have a relatively low dose deposition in the entrance region (plateau), followed by a steep increase to a dose (Bragg) peak, and an even steeper distal dose fall-off. The steep distal dose gradient of proton beams is particularly helpful in protecting these organs at risk. The reduction of range uncertainties offers proton therapy an advantage over x-rays. It results in proton therapy delivering less dose to healthy tissues, thus causing fewer complications and side effects, and resulting in a better quality of life for the patient. However, the steep distal dose fall-off and finite range of proton beams can also be a disadvantage when the patient's desired treatment location is uncertain. This uncertainty in treatment location may be due to several reasons.

For example, the use of x-ray imaging for treatment planning to obtain a map of relative stopping power (RSP) of tissues (relative to water) may be inaccurate due to the differences in the dependence of x-ray attenuation and proton energy loss on tissue composition (electron density and atomic number). This yields an inherently inaccurate conversion of x-ray Hounsfield units to proton RSP. There may also be uncertainties in patient setup, including alignment of the patient to the isocenter and deformations from non-rigid changes such as shoulder movements. Furthermore, changes in the position of a tumor during the patient's breathing cycle and anatomical changes of the patient during the course of fractionated treatments may increase the amount of uncertainty.

Current treatment planning procedures try to minimize the effects of these uncertainties by including uncertainty margins, selecting beam angles tangential to organs at risk, and using dose delivery technologies such as Pencil Beam Scanning (PBS) and intensity-modulated proton therapy (IMPT). In PBS, a beam of proton radiation is steered and focused on the treatment location, thereby reducing unnecessary radiation exposure to surrounding non-cancerous cells. In IMPT, two or three proton beams are combined during each treatment to deliver individual dose distributions that add up to a highly conformal dose in the target volume and a much lower dose to organs (e.g., eyes, cranial nerves, parotid glands) at risk. However, uncertainties increase the high-dose treatment volume and can preclude use of advantageous beam angles. Superior dose distribution and cost reduction in proton therapy can be achieved by using proton beam-based image guidance in procedures such as rapid online adaptive therapy. This technique is particularly helpful for hypo-fractionated treatments, which can benefit from more conformal dose distributions and a higher standard of safety given the high dose delivery for each treatment.

While performing treatment planning and dose delivery using the above techniques, the knowledge of the water equivalent path length (WEPL) of each ray, or pencil beam, from the skin to every point in the target is crucial. For protons, this length is estimated from RSP based on x-ray Hounsfield units. Unfortunately, such estimates lead to 3 to 4% uncertainties in the proton range prediction. Therefore, protons in the Bragg peak may overshoot (or undershoot) the desired stopping depth in the target causing tissue damage beyond the target volume.

The current algorithms for updating RSP maps with protons involve iteratively moving towards an improved solution under broad sets of conditions. However, these algorithms require reconstructed pRad images, which may be costly and time consuming, and limits the use of general proton data sets.

BRIEF SUMMARY

Described herein are improved systems and methods for performing deformable image reconstruction and/or updating relative stopping power (RSP) maps for pCT image reconstruction. The improved system and methods use individual proton measurement data (list-mode protons) without requiring use of an entire proton radiography (pRad) image. The individual proton measurements may comprise an arbitrary set of angles and/or positions. The disclosed pCT imaging system and associated reconstruction methods comprise an iterative method that moves towards the optimal solution, where each iteration is fast and efficient, and the number of iterations is minimized. The method offers a unique solution that optimally fits protons, while minimizing deviations from the original or deformed RSP map. The method also offers other advantages like being able to assign different deviation-associated weights to different voxels, as well as being able to account for correlations in the deviations between voxels; the ability to define a direction for each iteration that takes into account the noise in the proton data arising from measurement uncertainties; the ability to define an optimal step size for each iteration individually; the ability to simultaneously optimize the step sizes of many iterations; the ability to divide the proton data into an arbitrary numbers of blocks for parallel processing, where the blocks can be as small as a single proton; the ability to optimize computing resources; and the ability to define the stopping criteria for the iterations.

A method for proton radiation therapy treatment planning is disclosed. The method comprises: performing image registration to account for differences between an original image and an updated image; updating an original RSP map corresponding to the original image using individual proton measurement data, wherein the individual proton measurement data are associated with the updated image; comparing the updated RSP map to the original RSP map, wherein the original image corresponds to the original RSP map; and acquiring additional proton data in accordance with a difference between the updated RSP map and the original RSP map being greater than a pre-determined difference. Additionally or alternatively, in some embodiments, the performing image registration and the updating the original RSP map steps are performed without use of an entire proton radiography (pRad) image. Additionally or alternatively, in some embodiments, performing image registration comprises iteratively determining a deformation field based on a distance of a voxel deviation vector relative to a deformed template image prediction. Additionally or alternatively, in some embodiments, the method further comprises: determining the voxel deviation vector based on the individual proton measurement data and the original RSP map. Additionally or alternatively, in some embodiments, performing image registration comprises matching the original RSP map using individual proton trajectories or WEPL measurements. Additionally or alternatively, in some embodiments, updating the original RSP map comprises matching the individual proton measurement data to values of the original RSP map. Additionally or alternatively, in some embodiments, updating the original RSP map comprises assigning different uncertainties to different regions of the updated image. Additionally or alternatively, in some embodiments, updating the original RSP map comprises optimizing a deviation of the individual proton measurement data from values of the original RSP map. Additionally or alternatively, in some embodiments, the deviation comprises a voxel deviation or a proton deviation. Additionally or alternatively, in some embodiments, optimizing a deviation comprises: searching for minimums and maximums in the deviation; determining the relaxation parameter based on a magnitude of the deviation; determining a plurality of relationships between the deviation and the updated RSP map; determining a goodness of fit of the plurality of relationships; and repeating the searching and determining steps until a stopping criteria has been met, wherein the stopping criteria is associated with the determined goodness of fit. Additionally or alternatively, in some embodiments, searching for minimums and maximums in the deviation comprises, for each iteration, determining an updated RSP value and updating Lagrange multipliers. Additionally or alternatively, in some embodiments, determining the goodness of fit comprises performing a chi-square minimization process. Additionally or alternatively, in some embodiments, the stopping criteria comprises a root-mean-square of the deviation being less than a pre-determined precision value. Additionally or alternatively, in some embodiments, the method further comprises: assigning uncertainties or correlations to voxels in the updated RSP map using a covariance matrix. Additionally or alternatively, in some embodiments, the voxels in a region are assigned the same uncertainties or correlations. Additionally or alternatively, in some embodiments, the additional proton data indicate changes between the original RSP image and the updated RSP map. Additionally or alternatively, in some embodiments, the method further comprises: adapting a treatment plan based on the updated RSP map. Additionally or alternatively, in some embodiments, positions, angles, or both, of the original image are different than positions, angles, or both, respectively, of the updated image.

A system for proton computed tomography (pCT) image reconstruction is disclosed. The system comprises: a source for generating a pencil beam of protons; a scanning element for steering the pencil beam of protons; a plurality of tracking detectors for generating photons, the photons corresponding to the pencil beam of protons interacting with an object; a residual range detector; and a computing system for receiving signals from the plurality of tracking detectors and the residual range detector, the computing system configured to: perform image registration to account for differences between an original image and an updated image; update an original RSP map corresponding to the original image using individual proton measurement data, wherein the individual proton measurement data are associated with the updated image; compare the updated RSP map to the original RSP map, wherein the original image corresponds to the original RSP map; and acquire additional proton data in accordance with a difference between the updated RSP map and the original RSP map being greater than a pre-determined difference. Additionally or alternatively, in some embodiments, the computing system performs the image registration and the update of the original RSP map steps without use of an entire proton radiography (pRad) image.

It will be appreciated that any of the variations, aspects, features, and options described in view of the systems and methods apply equally to the methods and vice versa. It will also be clear that any one or more of the above variations, aspects, features, and options can be combined. It should be understood that the invention is not limited to the purposes mentioned above, but may also include other purposes, including those that can be recognized by one of ordinary skill in the art.

DETAILED DESCRIPTION OF THE INVENTION

Figure 1:
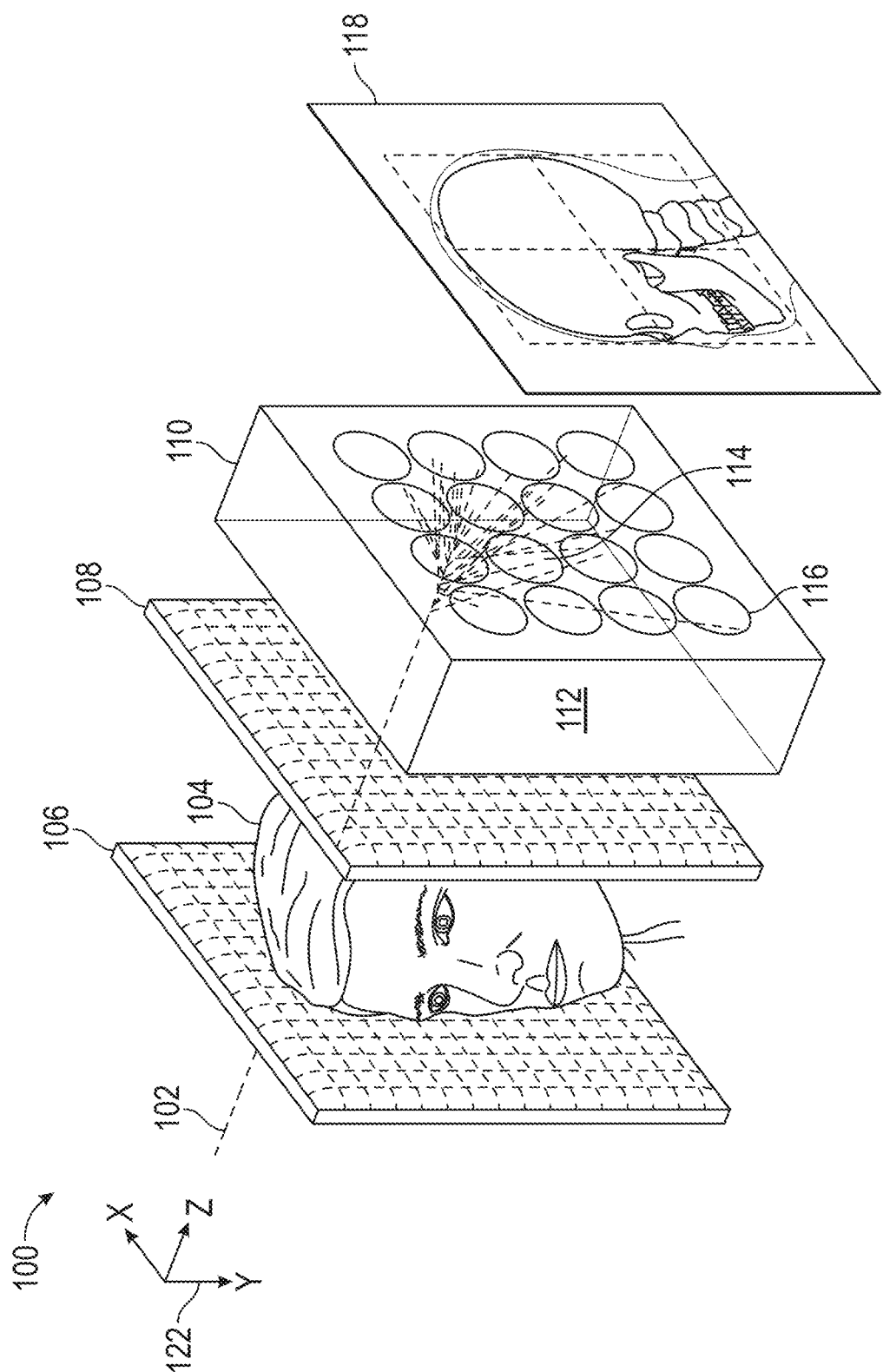
FIG. 1 depicts an example proton imaging system, according to some embodiments of the disclosure.

Embodiments of the disclosure comprise a method that uses individual proton measurement data (list-mode protons) for performing image registration and/or updating an RSP map for pCT image reconstruction. The disclosed image reconstruction and updating methods are capable of using protons from an arbitrary set of angles and positions (rather than starting from, e.g., pRad images). The methods comprise iterative reconstruction methods that move towards an optimal solution using iterations that are efficient, fast, and useful. The disclosed methods may be applied to clinical treatment planning, such as for adaptive planning.

In some embodiments, the updating methods may update an RSP map using a covariance matrix (e.g., instead of a weight matrix). The covariance matrix is used to account for different uncertainties. Uncertainties may be measurement uncertainties, as one non-limiting example, that create noise in the proton data. In some embodiments, uncertainties for different regions of the updated RSP map may be accounted for using the covariance matrix. Each iteration of the iterative reconstruction method may correctly take into account the noise in the proton data arising from measurement uncertainties, optimizing the overall fit of the RSP map to the proton data even though each proton does not fit perfectly due to measurement uncertainties. Additionally or alternatively, different weights for the deviations from the original or deformed RSP map may be assigned to different voxels. The different weights may account for correlations in the deviations between voxels.

Although the descriptions provided herein are in the context of a system for proton imaging, embodiments of the disclosure apply to other ions, such as helium, and/or other tomographic modalities, such as x-ray imaging. For example, a set of x-ray measurements from a few angles could be used to update a CT scan by describing each pixel of the x-ray measurements as a straight trajectory through the patient with a measurement of the attenuation along that trajectory. These pixels do not necessarily need to be organized into radiographs.

The following description is presented to enable a person of ordinary skill in the art to make and use various embodiments. Descriptions of specific devices, techniques, and applications are provided only as examples. These examples are being provided solely to add context and aid in the understanding of the described examples. It will thus be apparent to a person of ordinary skill in the art that the described examples may be practiced without some or all of the specific details. Other applications are possible, such that the following examples should not be taken as limiting. Various modifications in the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to a person of ordinary skill in the art, that one or more aspects and/or features described or referenced herein may be practiced without some or all of these specific details. In other instances, well-known process steps and/or structures have not been described in detail in order to not obscure some of the aspects and/or features described or referenced herein.

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combination of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

FIG. 1 depicts system 100, which is an embodiment of a proton imaging system according to the present disclosure. In some examples, a pencil beam 102 (alternatively, a broad beam could also be used with variations of the present technology) of protons (although other particles, such as heavy ions, could also be used) is generated or extracted from a source (e.g., source 202 of FIG. 2) and scanned across a field by a scanning element (e.g., scanning element 204 of FIG. 2). For example, pencil beam 102 is scanned across a region of interest of object 104, which is a human head in FIG. 1. The position of pencil beam 102 as it enters object 104 can be determined based on data from a tracking detector 106 that generates photons at locations where protons traverse the tracking detector 106. The position of pencil beam 102 as it exits object 104 can be determined using data from a tracking detector 108. Note that tracking detectors 106 and 108 are spaced apart to allow object 104 to be positioned between them. In some embodiments, only one tracking detector is needed, or two or more tracking detectors are used, on one or both sides of the object 104. For example, the tracking detectors 106 and 108 measure the transverse position of individual protons before and after the object 104. Embodiments comprise other architectures for tracking detectors 106 and 108.

Residual range detector 110 is positioned adjacent tracking detector 108. Residual range detector 110 includes scintillator material 112 (represented in FIG. 1 by a box). As a proton of pencil beam 102 enters scintillator material 112 through the surface facing tracking detector 108, the proton generates photons 114 (represented by dotted lines in FIG.

1) as the protons lose energy from interacting with scintillator material 112. These photons can then be collected by photon detectors (e.g., photon detector 224 of FIG. 2) coupled to scintillator material 112. The photon detectors may be coupled to the surface of scintillator material 112 that is opposite the surface facing tracking detector 108. The coupling of the photon detectors is depicted in FIG. 1 by circles 116. The signal generated by the photon detectors is proportional to a residual energy of a proton as it entered scintillator material 112. This information combined with the initial energy of the proton and the location of the proton as it entered and exited object 104, along with similar information for many additional protons, can be used to generate image 118 of object 104. Stated differently, the residual range detector 110 determines the proton energy absorbed with the object 104. By using multiple proton energies and/or protons at different angles (e.g., 100 different angles) in a proton tomography system using the present technology, 3D images can be produced.

Figure 2:
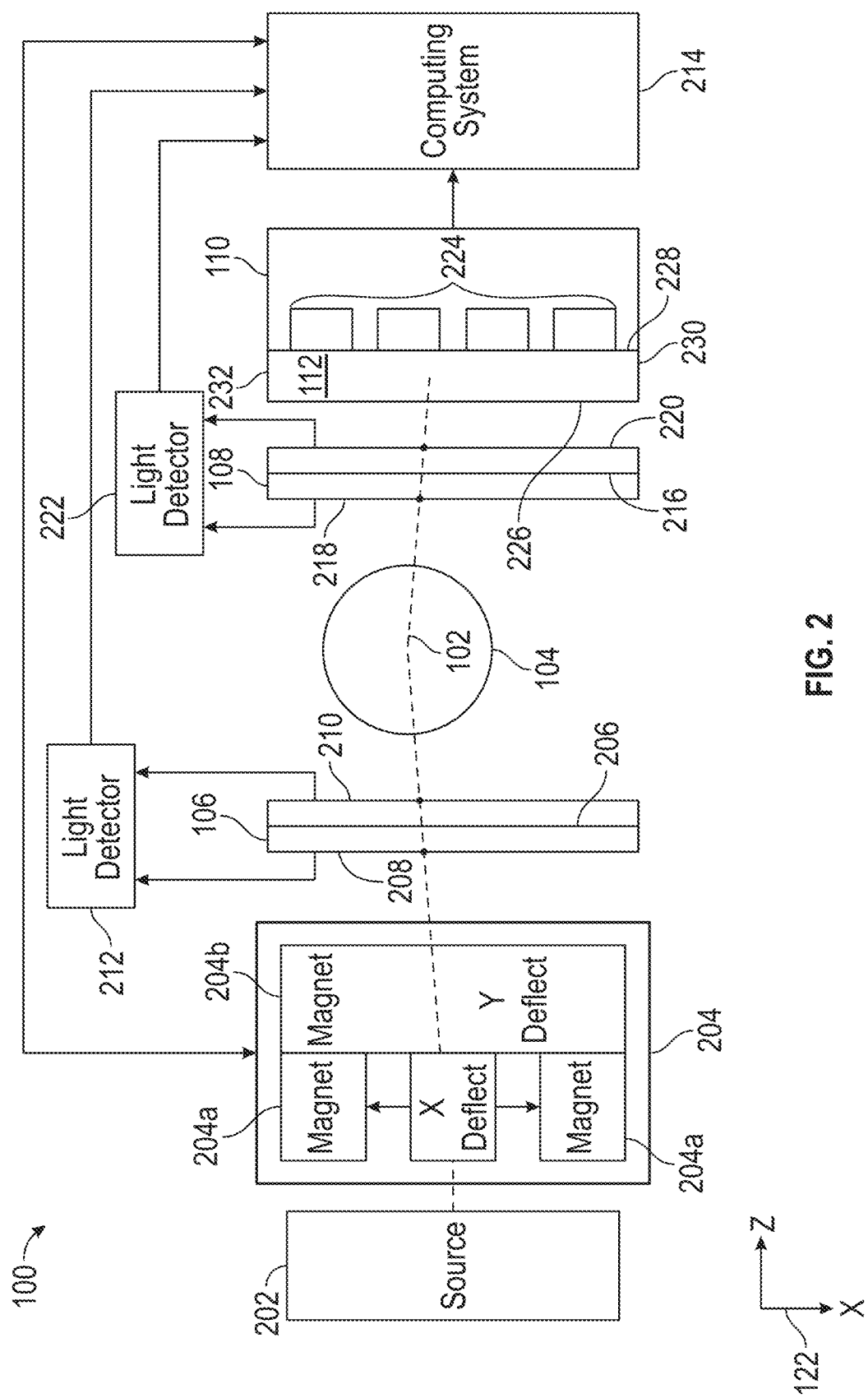
FIG. 2 depicts an example proton imaging system with additional detail and from a different perspective, according to some embodiments of the disclosure.

Note that reference axes 122 show that pencil beam 102 is traveling along the z-axis and tracking detectors 106 and 108 are perpendicular to the z-axis. FIG. 2 described below is described with respect to the same reference axes.

FIG. 2 depicts system 100 of FIG. 1 with additional detail and from a different perspective, as indicated by reference axes 122. With reference to FIG. 2, system 100 includes source 202 that generates or extracts pencil beam 102. Scanning element 204 is used to steer pencil beam 102 and includes scanning magnets 204a and 204b. Scanning magnets 204a scan the pencil beam 102 in x-directions as defined with respect to reference axes 122, and scanning magnets 204b (the second of which is hidden in the perspective of FIG. 2) scan pencil beam 102 in y-directions, as defined with respect to respect to reference axes 122. In general, scanning element 204 is programmable such that pencil beam 102 is scan-able across the entirety of the field in any pattern, and, as determined by source 202, at any initial energy at any point in time. In this example, source 202 is capable of controlling or varying the initial energy of the protons of pencil beam 102. During a scan, the extent of the field is in general limited by the planar dimensions of first tracking detector 106, second tracking detector 108, or residual range detector 110 of system 100. Example field areas include 10×10 cm$^2$ to 38.4×38.4 cm$^2$.

By using a different initial energy at different transverse positions of the tracking detectors and the object being imaged, the depth of the residual range detector can be kept small. For example, the initial energies can be chosen to keep the residual range between 0 and 10 cm across the field to be imaged regardless of the thickness or density of the object along a particular path. The more range in initial energy that is possible, smaller residual range detectors may be possible.

In some examples of an architecture for tracking detector 106, as protons of pencil beam 102 traverse first tracking detector 106, the protons interact with fibers on either side of substrate 206. Specifically, each side of substrate 206 includes, for example, two layers of fibers, e.g., fibers 208 on one side and fibers 210 on the opposite side of substrate 206. Fibers 208 and 210 may be scintillating fibers so that when a proton impinges a fiber, the scintillating properties of the fiber may cause one or more photons to be generated. These photons are captured by light detector 212, which generates an electrical signal based on the detected photons. The electrical signal is transmitted to computing system 214. By knowing the location and orientation of fibers 208 and 210 that produced photons, the location of the proton that traversed tracking detector 106 may be determined by computing system 214. Additionally, computing system 214 may also use data from scanning element 204 to determine or verify the location where a proton passed through tracking detector 106. Once the location is known, the initial directional vector of pencil beam 102 can also be determined based on the focal point of source 202.

As protons of pencil beam 102 traverse object 104, protons may be scattered, as is depicted in FIG. 2 as an exaggerated change in direction of pencil beam 102 in object 104. After the protons exit object 104, the exit location where protons traverse tracking detector 108 can be determined in a similar manner as described above with respect to tracking detector 106. Similar to tracking detector 106, the tracking detector 108 includes fibers on substrate 216. Specifically, each side of substrate 216 includes, for example, two layers of fibers, e.g., fibers 218 on one side and fibers 220 on the other side of substrate 216. Fibers 218 and 220 may be scintillating fibers so that when a proton impinges a fiber, the scintillating properties of the fiber may cause one or more photons to be generated. These photons may be captured by light detector 222, which may generate an electrical signal based on the detected photons. The electrical signal is transmitted to computing system 214. By knowing the location and orientation of fibers 218 and 220 that produced photons, the location of the proton that traversed first tracking detector 108 may be determined by computing system 214. Additionally, computing system 214 may also use information from scanning element 204 to determine or verify the location on tracking detector 108 where a proton passed through the tracking detector 108.

In some examples, fibers 218 are oriented perpendicular to fibers 220. If light detector 222 indicates that a proton passed through one fiber of fibers 218 and one fiber of fibers 220, and computing system 214 knows the location of these two fibers, then computing system 214 can determine that the X-Y coordinate on tracking detector 108 where the proton traversed tracking detector 108 is at the intersection of the two fibers. Additionally, if fibers of fibers 218 or fibers of fibers 220 are connected together to reduce the number of detectors needed in light detector 222, then the estimated or expected position of pencil beam 102 based on data from or instruction sent to scanning element 204 may be used in determining the X-Y coordinate on tracking detector 108 where the proton traversed tracking detector 108.

While an exemplary architecture of a tracking detector has been described, embodiments of the disclosure may include other architectures. For example, if fibers are rigid enough, the fibers could be bonded together to avoid using a substrate. As another example, with respect to tracking detector 106, fibers 208 and 210 could be placed on the same side of substrate 206 or fibers 208 and 210 could be placed on separate substrates that are placed next to each other.

As protons of pencil beam 102 enter residual range detector 110, they impinge scintillator material 112 and generate photons that are collected by photon detectors 224 (while four photon detectors are depicted in FIG. 2, system 100 includes sixteen photon detectors as indicated by the circles representing the photon detectors couplings to scintillator material 112 in FIG. 1). Photon detectors 224 are, for example, photomultiplier tubes or other similar devices. Photon detectors 224 generate electrical signals based on the number of photons collected and generate electrical signals that are provided to computing system 214, which may calculate values such as total energy. Based on the electrical signals, and potentially other information (such as the X-Y coordinate of where a proton exited object 104 and traversed tracking detector 108), computing system 214 may determine a residual energy for a proton of pencil beam 102 that entered scintillator material 112 after exiting object 104.

Protons enter scintillator material 112 via surface 226. Generated photons are collected by photon detectors 224 as the photon exit surface 228 of scintillator material 112. The dimensions of scintillator material 112 may be selected to ensure that protons stop in scintillator material 112 as opposed to passing through scintillator material 112. This ensures that protons of pencil beam 102 generate a large number of scintillation photons within a few nanoseconds. Surface 226, surface 230, surface 232, and/or the other two surfaces of scintillator material 112 not depicted in FIG. 2 are, in some examples, covered (e.g., deposited, coated, or arranged next) with an anti-reflective or photon absorbing material. For example, the walls of scintillator material 112 are painted black. The anti-reflective material ensures that mainly direct photons that have not scattered off the walls of scintillator material 112 are collected at photon detectors 224. The anti-reflective material may include different materials on different surfaces of scintillator material 112. The anti-reflective material may absorb 90% or more of the photons that contact the material. The anti-reflective material adds to the high speed operation of system 100.

The use of multiple photon detectors also provides the potential to obtain additional position data for the location that a proton exited object 104. For example, with reference to FIG. 1, if photon detectors are coupled to scintillator materials 112 as indicated by circles 116 (sixteen total), the photon detector nearest where the photon entered scintillator material 112 should produce the strongest signal. If the position of the photon detector that produces the strongest signal does not correlate with the position indicated by the signals generated from tracking detector 108 and light detector 222, then an event that should be rejected may exist, such as inelastic scatter.

Figure 3:
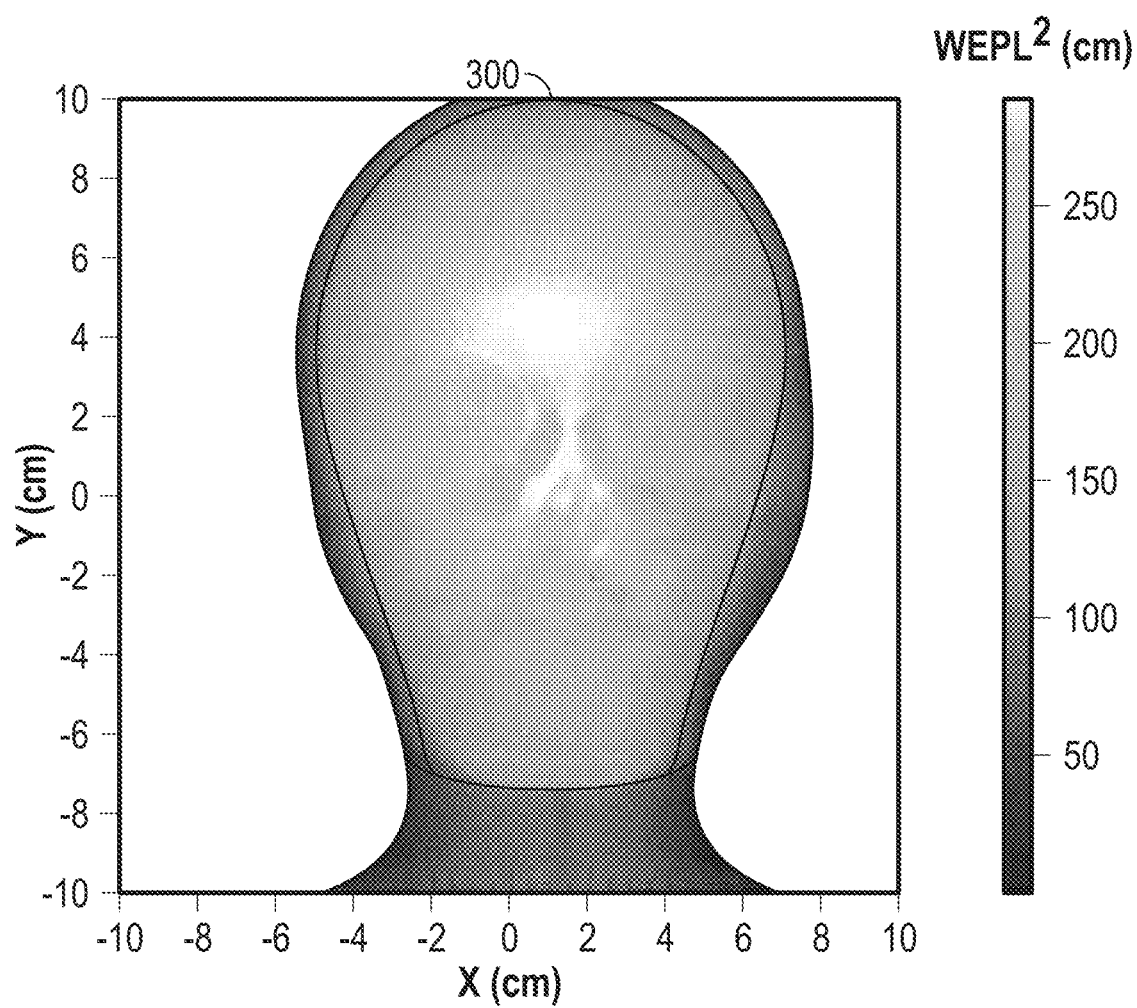
FIG. 3 illustrates a proton radiography (pRad) image using data taken with multiple incoming proton energy beams, according to some embodiments of the disclosure.
Figure 4A:
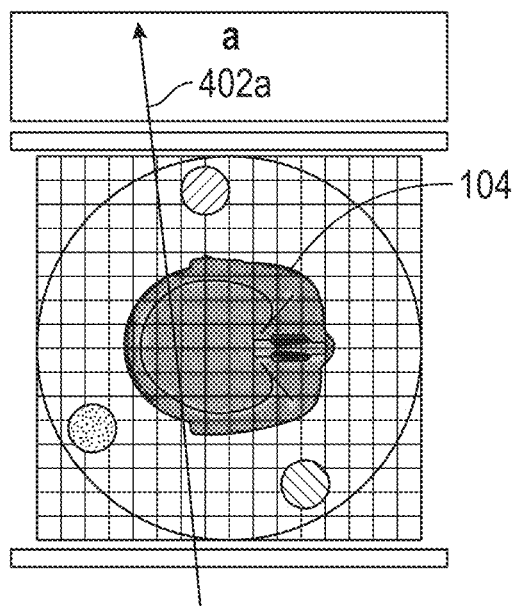
FIGS. 4A-4D illustrate examples of the different angles used for construction of a 3D proton computed tomography (pCT) image, according to some embodiments.
Figure 4B:
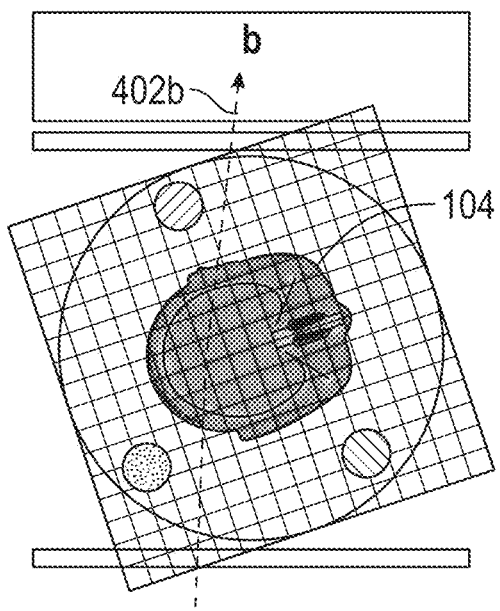
Figure 4C:
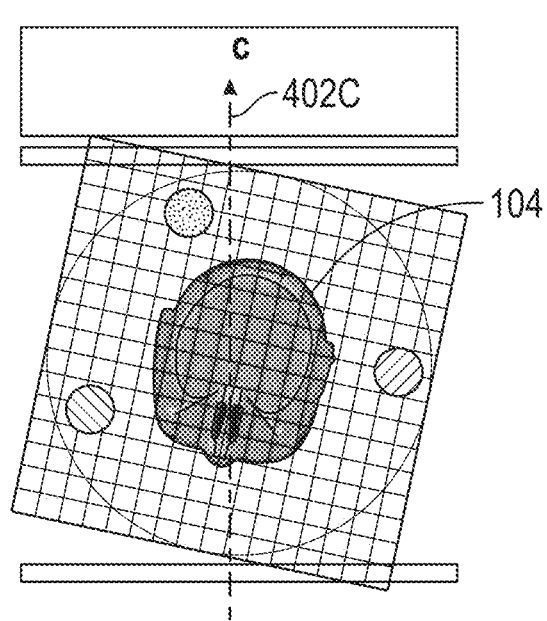
Figure 4D:
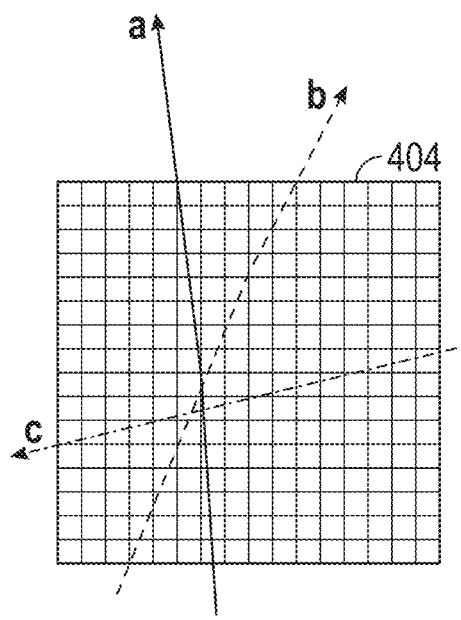

FIG. 3 illustrates a proton radiography (pRad) image using data taken with multiple incoming proton energy beams. A two-dimensional pRad image uses a single projection angle, directly quantifying proton range through the object 104 (e.g., a patient) rather than integrated x-ray attenuation. In some examples, the system 100 may be used to reconstruct a 3D pCT image by obtaining multiple images corresponding to multiple proton beams at different angles. To reconstruct the image 300, a 3D RSP map of the object 104 may be built by acquiring proton histories from a full set of projection angles.

FIGS. 4A-4D illustrate examples of the different angles used for construction of a 3D pCT image. For example, protons 402a, 402b, and 402c may interact with the object 400 at different angles relative to detectors 106 and 108. For image reconstruction, the trajectories of protons 402a, 402b, and 402c may be placed in a single 3D coordinate grid 404, which may move with the object 104. In some examples, markers on a rotating platform can help determine the rotation angle, used optionally with optical tracking, to transform the detector coordinates to the reconstruction grid.

Proton beam trajectories may deviate from straight lines due to multiple Coulomb scattering, which may blur images. In some examples, this limitation can be overcome by measuring each proton trajectory individually to estimate its most likely path, along with its energy loss quantified as WEPL, and then applying iterative reconstruction algorithms. One challenge for pCT is to acquire protons through the object 104 at many different angles and put all proton trajectories into a single 3D coordinate grid for image reconstruction, as illustrated in FIGS. 4A-4D. After obtaining the data from multiple protons beams, the iterative reconstruction algorithms may be used to adjust the RSPs of the voxels touched by the protons to match the residual range of protons. In some examples, the iterative reconstruction algorithms to reconstruct the images may be implemented using parallel processing on central processing unit (CPU)/general processing unit (GPU) computers. In some embodiments, computing resources (e.g., GPUs) may be optimized. Additionally or alternatively, data acquisition and image reconstruction may be combined to promptly display images accurately in terms of water equivalent thickness (WET) or RSP.

One use for proton imaging is adaptive planning. A treatment plan based on an RSP map may be modified based on new proton imaging data taken with a patient just before treatment, for example. Modifications may be needed because the treatment plan may comprise an x-ray CT scan (rather than a pCT), there may have been anatomical changes in the patient since the treatment plan was developed, and/or the patient might not have the same exact positioning as for the original RSP map used for the treatment plan.

Figure 5A:
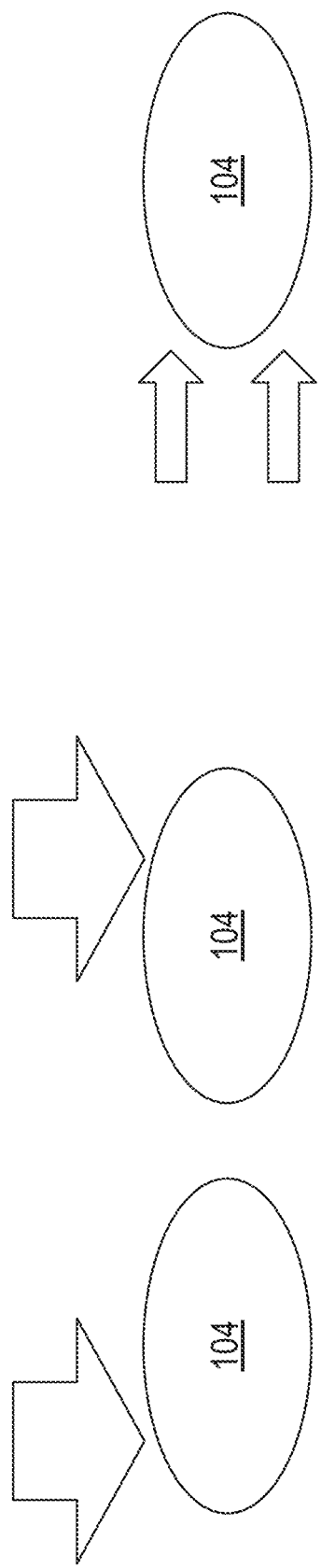
FIGS. 5A-5C illustrate example data for adaptive planning that may not be suitable for pRad or pCT images, according to some embodiments.
Figure 5B:
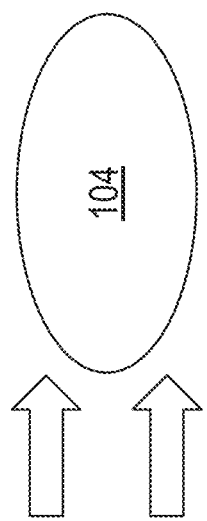
Figure 5C:
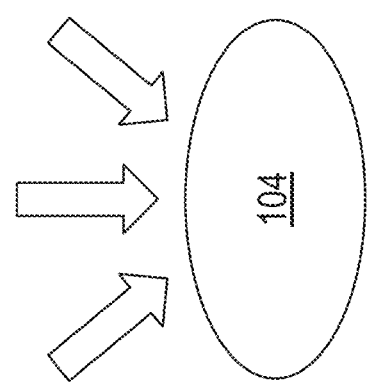

In some embodiments, the data for adaptive planning (updated image) may come from an arbitrary set of positions and/or angles (different from the original image). FIGS. 5A-5C illustrate example data for adaptive planning that may not be suitable for pRad or pCT images, according to some embodiments. pRad uses a single direction, and pCT requires a complete set of positions and angles. As one example, the object 104 may be larger than the imaging field (FIG. 5A), resulting in data representing only a limited region. As another example, the data may comprise only data for the edges due to the protons not having enough energy to penetrate the object 104 for all positions in one direction (FIG. 5B). Additionally or alternatively, as shown in FIG. 5C, the data may be from a few angles focused only on the treatment region. There may be some missing positions or angles if there is not enough proton energy to traverse the object 104 in some directions, there may be several pRads, or there may be a complex assortment of positions and angles.

Figure 6B:
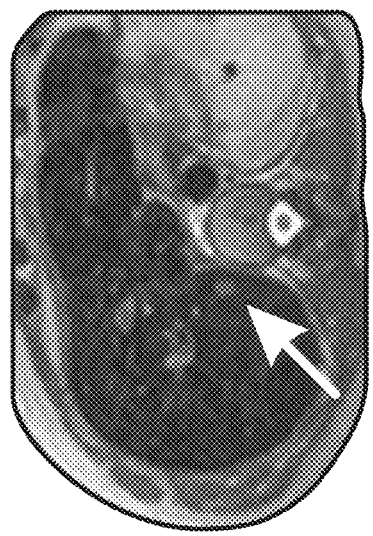
FIGS. 6A-6C illustrate example applications, according to some embodiments.
Figure 6C:
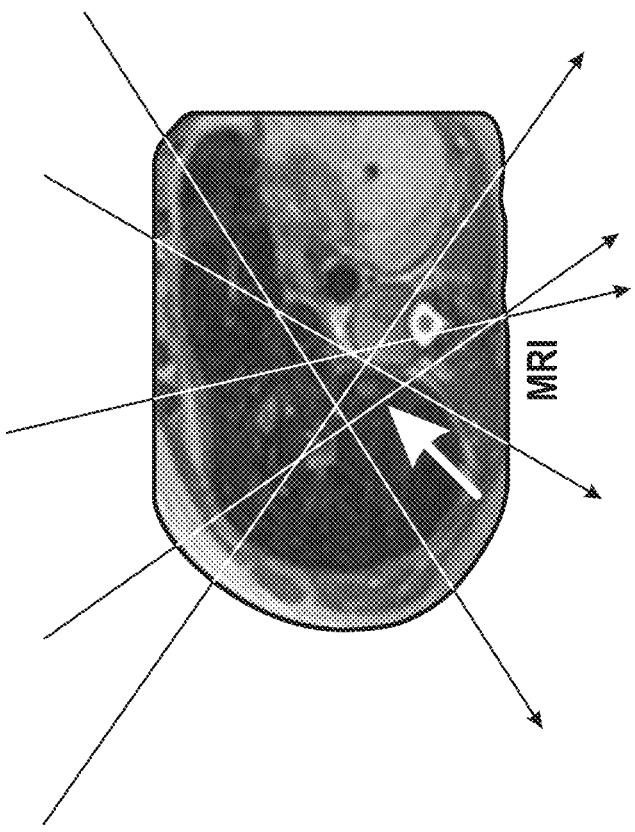
Figure 6A:
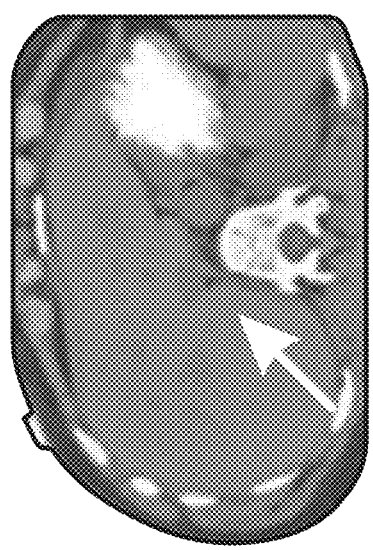

FIGS. 6A-6C illustrate example applications of the disclosed embodiments. A tumor may be difficult to detect in a CT scan (FIG. 6A), but may be visible in an MRI scan (FIG. 6B). In some embodiments, as shown in FIG. 6C, a large set of protons from many directions focused on the treatment region may be used to try to confirm, just before treatment, the location of a tumor previously seen only in MRI images.

Figure 7C:
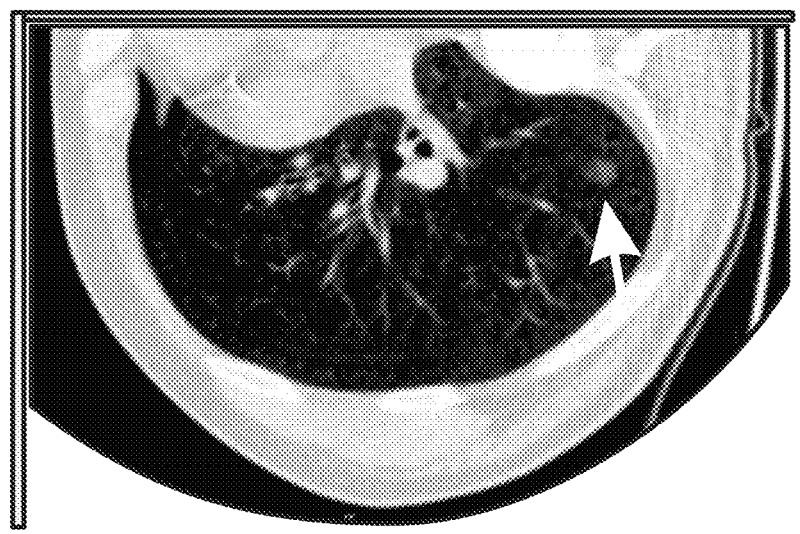
FIGS. 7A-7C illustrate a lung tumor growing in size with repeat images, according to some embodiments.
Figure 7B:
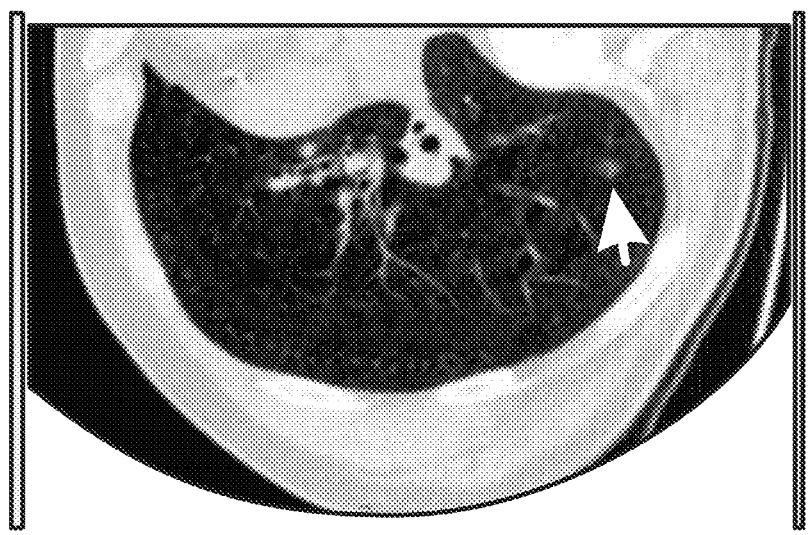
Figure 7A:
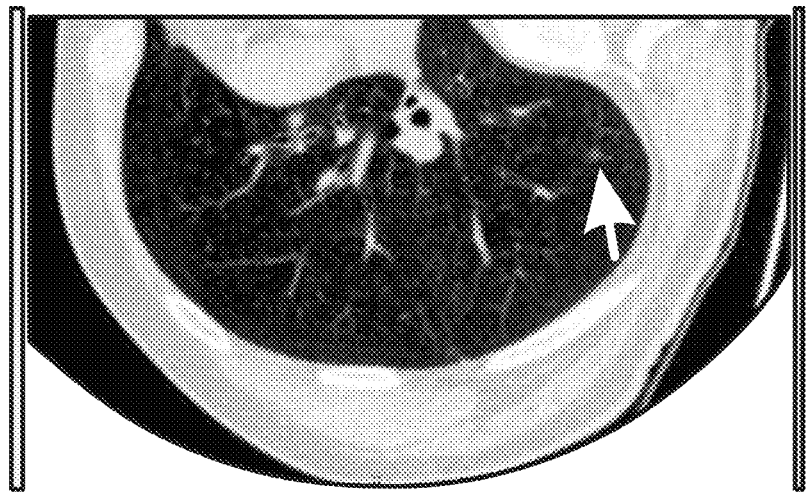

These methods may also be used for improved cancer screening, which also looks for changes in the patient. For example, FIGS. 7A-7C illustrate a lung tumor growing in size with repeat images. Instead of taking an entire CT scan for each repeat image (as is typical in low-dose CT lung cancer screening), the systems and methods disclosed herein allow the use of a select set of angles and positions with reduced dose. This would enable more frequent repeat images to be taken, and additional data focused on areas of concern, such as possible tumor candidates to be monitored. Another non-limiting example application of the disclosed systems and methods include monitoring the build-up of plaque in arteries and development of atherosclerosis.

Figures 8A, 8B:
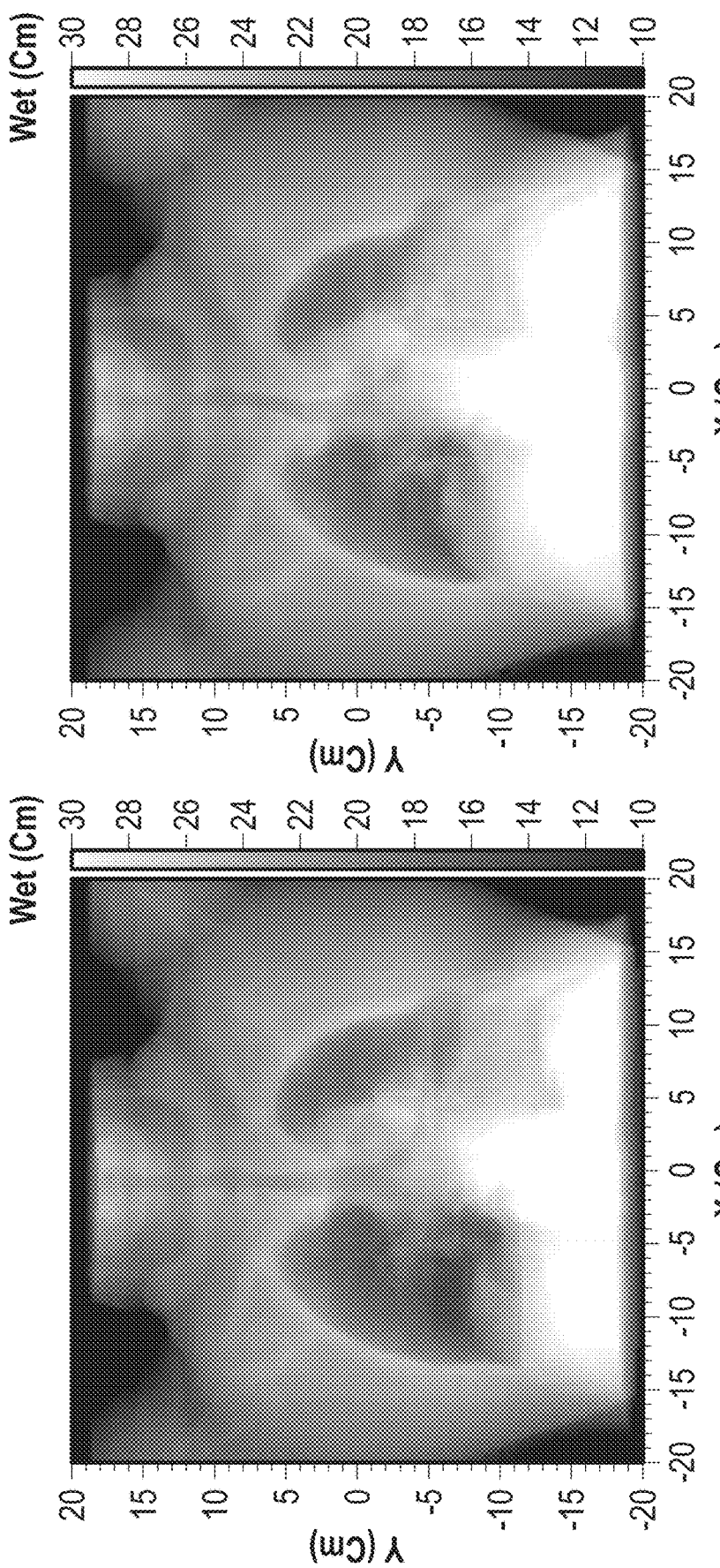
FIGS. 8A and 8B illustrate example patient anatomy changes during a breathing cycle, according to some embodiments.

These methods may also be used for motion management. FIGS. 8A and 8B illustrate example patient anatomy changes during a breathing cycle. Data taken at different times during the breathing cycle may be used with the image registration (e.g., deformable image registration (DIR)) and update (e.g., RSP map update) methods disclosed herein to understand changes in the RSP map during the breathing cycle. Small pRads with a single energy, for example, using one million or fewer protons in a 10 cm by 10 cm area, can be performed very quickly (e.g., in less than 0.1 seconds, in some cases). This would enable a quick snapshot of the patient to verify that the patient is in the proper phase of the breathing cycle planned for the treatment, just before the treatment is delivered.

Exemplary Method for Adaptive Treatment Planning

Figure 9:
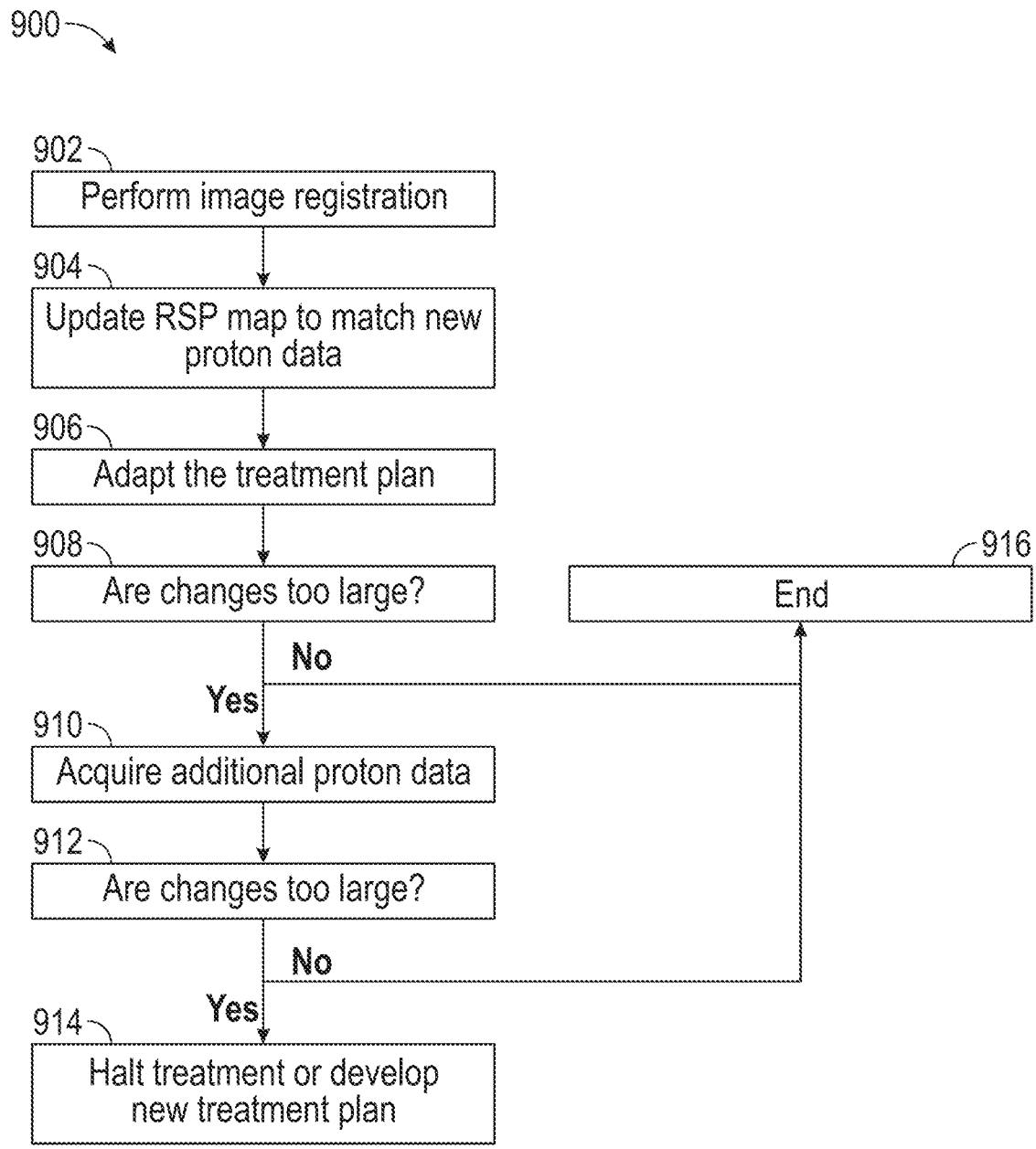
FIG. 9 illustrates a flowchart for an example treatment plan adaptation method, according to some embodiments.

FIG. 9 illustrates a flowchart for an example treatment plan adaptation method, according to some embodiments. The treatment plan adaptation method may be implemented before treatment. Method 900 comprises performing image registration (e.g., deformable image registration (DIR)) in step 902. The image registration step comprises determining the differences between a plurality of images so that they are mapped onto the same coordinate system. For example, the plurality of images comprises an original image (e.g., x-ray) and an updated image (e.g., CT scan). In some embodiments, the image registration in step 902 may match the original RSP map used for treatment planning to the position, orientation, and/or anatomical distortions of the object 104. In step 904, the RSP values of the original or deformed RSP map are updated to match the individual proton measurement data (e.g., new proton data comprising list-mode proton data). An example RSP update method is described in more detail below.

Step 906 comprises adapting the treatment plan based on a comparison between the updated RSP map (from steps 902 and 904, respectively) and the original RSP map (corresponding to the original image). If the changes are too large (for example, change of 10 mm or more in the range to the tumor, a target reliability in the range to the tumor of 2 mm, or an analysis indicates that the uncertainties on the correction are larger than this) (determined in step 908 by the differences between the updated RSP map and the original or deformed RSP map not meeting a pre-determined criteria), additional proton data may be acquired (step 910). The additional proton data may clarify the nature of the changes and/or improve the reliability of the updates. For example, additional proton data could indicate changes to an object (of the original image and the updated image), such as whether the changes between the two images occurred before or after the tumor in the treatment direction. In step 914, if the changes are still too large after acquiring additional proton data (determined in step 912), then the system may recommend halting treatment or developing a new treatment plan. If the charges are not large (as determined in step 908 or 912), the method 900 may end (step 916).

In this manner, the treatment plan adaptation method comprises performing image registration and updating the RSP map using individual proton measurement data (list-mode proton data). The individual proton measurement data that may comprise any proton data with no restrictions or requirements on the positions and angles of the protons. This is unlike conventional image registration methods that use pRad images, deforming a 3D distribution to conform one or more 2D projections. Conventional image registration methods do not use individual proton measurements data, but instead, rely on reconstructed pRad images. Since only individual proton measurement data are needed to update the RSP map, methods of the embodiments are faster, simpler, and require less resources and processing (e.g., memory, computations, etc.) then conventional methods for reconstructing a CT image.

Method 900 further differs from conventional RSP update methods in that it does not require a weight matrix, which is needed in chi-squared calculations. Instead, examples of the disclosure use a covariance matrix (the inverse of the weight matrix), where different uncertainties may be assigned to different regions of the update image. If, for example, some tissues are known to have larger uncertainties, the RSPs for regions with these tissues can be assigned larger uncertainties, and therefore these RSPs will be varied more in the update. As a result, less dose may be delivered to different regions depending on the uncertainties, leading to fewer complications and side effects and/or the ability to take more data on certain regions of interest.

Additionally or alternatively, the covariance matrix may specify and/or adjust correlations between voxels within a region. Conventional RSP update methods seek to minimize a combination involving a total variation voxel-to-voxel term and differences from the original RSP map. For example, in a conventional RSP update method, the differences from the original RSP map uses a weight matrix. In some embodiments, the weight matrix is the inverse of a covariance matrix describing the covariance between the RSP values of the voxels of the original RSP map. A parameter is chosen and tuned to set the relative sizes of the terms contributing to the combination being minimized. On the other hand, the disclosed systems and methods do not require a total variation term. These methods are also able to use a complex covariance matrix, which could be difficult to invert to obtain the weight matrix. Since the RSPs of voxels with the same tissue type can have correlated uncertainties, the use of correlation coefficients (used in the off-diagonal elements of the covariance matrix) in a region can be used to ensure these voxels are updated in a correlated way, using the data more efficiently than if each voxel were updated independently.

Example Method for Image Registration

In some instances, it may be beneficial to perform image registration, e.g., before updating the RSP map. Conventional methods perform a rigid registration for patient setup, which accounts for the main positioning in terms of translations and rotations. A deformable image registration (DIR) step may then account for any remaining differences, which may arise from anatomical changes, differences between supine and upright shape, small differences in limb positions or torso twisting, etc. The DIR step does not change the RSP values, but rather repositions the voxels to match major features in the current patient geometry.

Unlike conventional methods that use the distance of the reference data relative to a deformed template image prediction, embodiments of the disclosure uses the distance $D_u$ of the voxel deviation vector $d_v$ vector (relative to a deformed template image prediction), thereby allowing a non-rigid image registration from matching the original RSP map using individual proton trajectories and WEPL measurements. The data does not need to be organized into radiographs, and the registration can be more general than a 2D-3D registration. The image registration method of the present disclosure may be expressed as:

$$D_u = d_v \quad (1)$$

$$d_v(x)\nabla T(x-u(x)) + \alpha \Delta^2[u](x) = 0 \quad (2)$$

where $T(x-u(x))$ refers to the deformed image, $u(x)$ is the deformation field, and $\alpha$ is an empirically chosen parameter to balance limiting curvature (maintaining smoothness) of the deformation field with an optimal fit to the data. The image registration method comprises iteratively determining a deformation field $u(x)$ based on the distance $D_u$, with each iteration updating $D_u$ based on the revised $u(x)$. This use of the voxel deviation vector $d_v$ as the distance $D_u$ enables protons from an arbitrary set of positions and angles to be used for the image registration of the embodiments of the disclosure.

Figure 10:
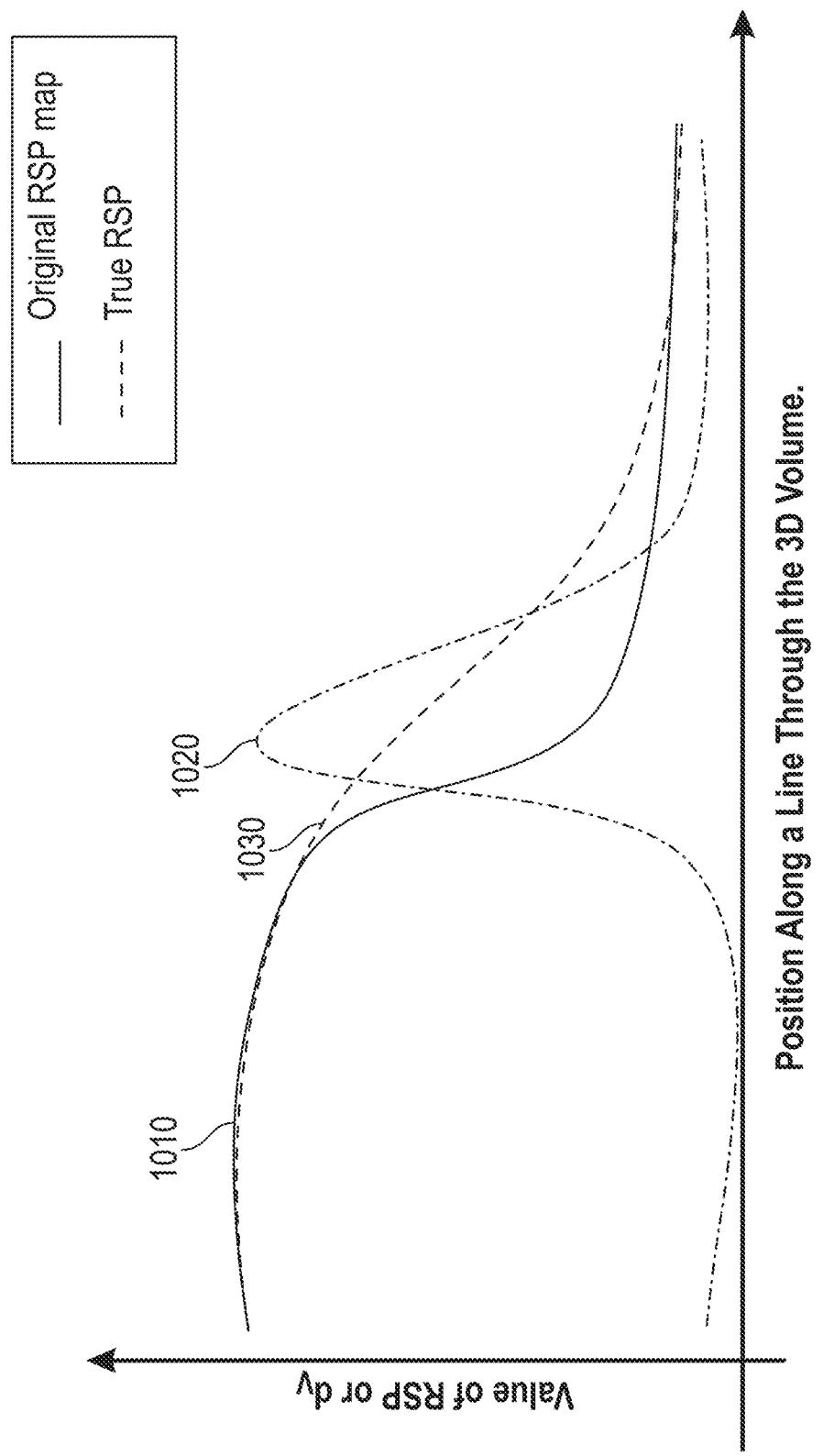
FIG. 10 illustrates an example plot comparing an original RSP map and a true RSP map, according to some embodiments.

FIG. 10 illustrates an example plot comparing an original RSP map 1010 and the true RSP map 1030 (for example, the actual RSP map of a patient at the time of treatment, which has changed since the original treatment plan), according to some embodiments. The true RSP map is not known, and the goal is to use new proton data to register the original RSP map to the true RSP map. The change in the map causes new proton data to have a non-zero $d_v$. As the plot shows, the image intensity gradient (slope of the original RSP curve) combines with new voxel deviation vector $d_v$ data to produce the image deformation to the right. In the example, the true RSP for the current patient setup has a distortion relative to the original RSP map used for treatment planning. The voxel deviation vector $d_v$ is determined based on new proton data (at the time of treatment) reflecting the true RSP map, resulting in a non-zero peak coinciding with the gradient of the deformed image 1020.

Example Method for Updating RSP Values

Embodiments of the disclosure comprise using a partial set of angles and positions to update an RSP map $x_x$. The partial set of angles and positions may be a subset of the full set of angles and positions in an image (e.g., a pRad image, a CT scan, etc.), for example. In some embodiments, the original RSP map $x_x$ may be an x-ray CT scan. The original RSP may comprise a few million voxels. A pCT image may comprise a few hundred million protons, each with a WEPL measurement with, e.g., approximately 3 mm uncertainty.

Figure 11:
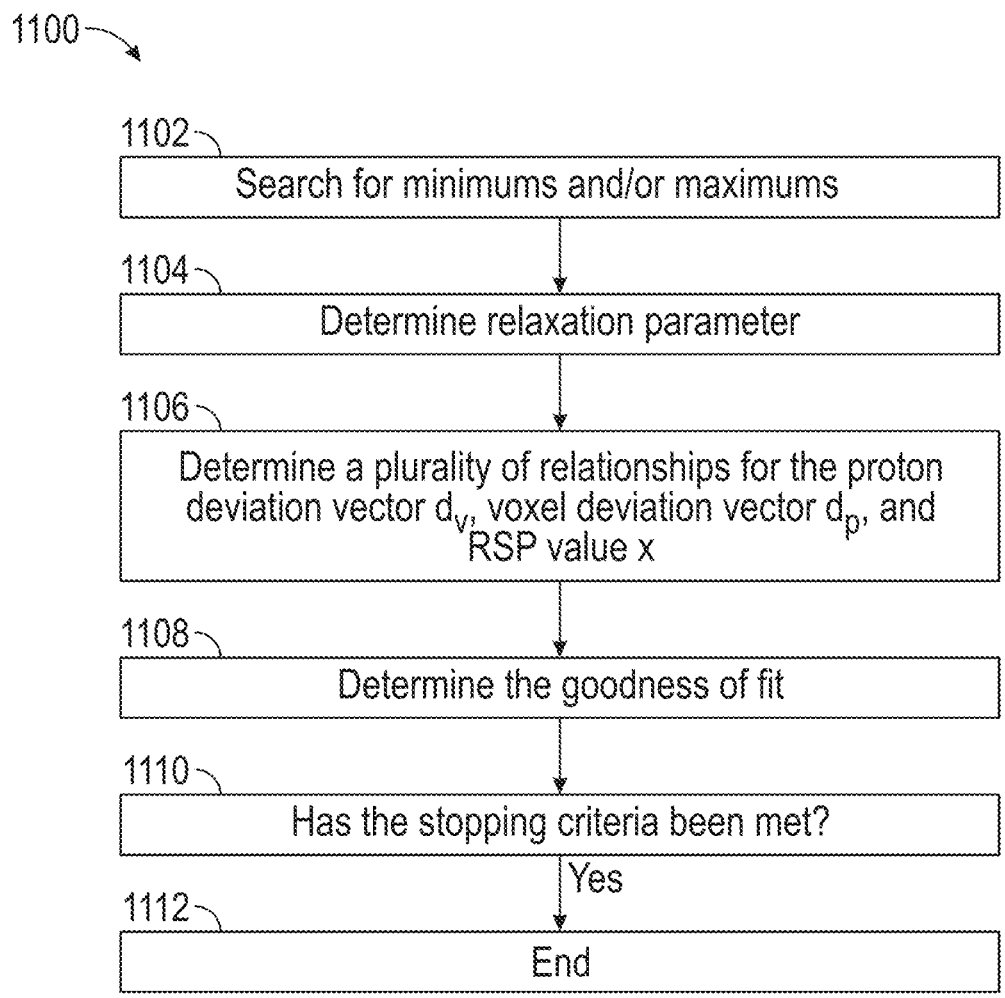
FIG. 11 illustrates a flowchart for an example method for updating am RSP map (e.g., step 904), according to some embodiments.

FIG. 11 illustrates a flowchart for an example method for updating am RSP map (e.g., step 904), according to some embodiments. Method 1100 comprises optimizing the deviation of the updated RSP map from the original or deformed RSP map $x_x$. The optimization process may comprise finding a solution with the smallest proton deviation vector $d_p$ or voxel deviation vector $d_v$ among the individual proton measurement data (protons going through the voxels), for example. In some embodiments, minimizing the deviation comprises imposing a constraint that the voxel deviation vector is zero: $d_v=0$. The voxel deviation vector $d_v$ may be expressed as a weighted average of the proton deviation vector $d_p$ of the protons going through the voxel:

$$d_v = \overline{A}^T d_p \quad (3)$$

where:

$$\overline{A}^T = V^{-1} A^T \quad (4)$$

$$V^{-1} = \text{diag}(1/\Sigma_j \alpha^T_{ij}) \quad (5)$$

$$d_p = Ax - b \quad (6)$$

The $\alpha$ are elements of the matrix A. In some embodiments, the proton deviation vector $d_p$ may be a non-zero value.

Step 1102 may comprise searching for minimums and/or maximums. In some embodiments, the search in step 1102 may include using Lagrange multipliers (to find a solution that minimizes the deviation from the original RSP map $x_x$) while imposing the constraint $d_v=0$. The Lagrangian solution may be expressed as:

$$L(x,y) = (x-x_x)^T W(x-x_x) + y^T d_v \quad (7)$$

where y is a vector of Lagrange multipliers, and W is a weight matrix (the inverse of a covariance matrix V).

The first term $(x-x_x)^T$ defines a goodness of fit constraint (determined in step 1108) on the deviation from the original RSP map, and the covariance matrix V allows voxels in different regions of the updated RSP map to be assigned different uncertainties. In some embodiments, the covariance matrix V defines correlations in the uncertainties between voxels.

The solution to the Lagrangian may be a saddle-point where the gradients are zero. This can be expressed as:

$$g_x = \partial L / \partial x = 2W(x-x_x) + y^T \overline{A}^T A = 0 \quad (8)$$

$$g_y = \partial L / \partial y = d_v = \overline{A}^T (Ax - b) = 0 \quad (9)$$

$$\begin{pmatrix} 2W & A^T \overline{A} \\ \overline{A}^T A & 0 \end{pmatrix} \begin{pmatrix} x \\ y \end{pmatrix} = \begin{pmatrix} 2Wx_x \\ \overline{A}^T b \end{pmatrix} \quad (10)$$

An iterative method, such as Uzawa's iterative method, may be used to solve the matrix of (10). The iterative method may involve, for each iteration k, determining the RSP value x and then updating the vector of Lagrange multipliers y.

$$x_k = \frac{1}{2} W^{-1} (2Wx_x - A^T \overline{A} y_k) \quad (11)$$

$$x_k = x_x - \frac{1}{2} W^{-1} A^T \overline{A} y_k \quad (12)$$

$$y_{k+1} = y_k + \lambda_k (\overline{A}^T A x_k - \overline{A}^T b) \quad (13)$$

$$y_{k+1} = y_k + \lambda_k \overline{A}^T d_{pk} \quad (14)$$

$$y_{k+1} = y_k + \lambda_k d_{vk} \quad (15)$$

where $\lambda$ is a relaxation parameter. In some embodiments, the initial Lagrange multiplier may be set as: $y_0=0$.

As shown above, embodiments of the disclosure comprise using a covariance matrix V, instead of inverting it to obtain the weight matrix W itself. In the following, we substitute V for $W^{-1}$. For a given iteration k, the RSP value $x_k$, voxel deviation vector $d_p$, proton deviation vector $d_v$, and Lagrange multiplier are:

$$x_k = x_x - \frac{1}{2} V A^T \overline{A} y_k \quad (16)$$

$$d_{pk} = Ax_k - b = d_{px} - \frac{1}{2} A V A^T \overline{A} y_k \quad (17)$$

$$d_{vk} = \overline{A}^T d_{pk} = d_{vx} - \frac{1}{2} \overline{A}^T A V A^T \overline{A} y_k \quad (18)$$

$$y_{k+1} = y_k + \lambda_k d_{vk} \quad (19)$$

In step 1104, the relaxation parameter $\lambda$ may be determined. In some embodiments, the optimal relaxation parameter may be determined $\delta$ vectors as:

$$\delta_{xk} = \frac{1}{2} V A^T \overline{A} d_{vk} \quad (20)$$

$$\delta_{pk} = A \delta_{xk} \quad (21)$$

$$\delta_{vk} = \overline{A}^T \delta_{pk} \quad (22)$$

$$x_{k+1} = x_x - \frac{1}{2} V A^T \overline{A} (y_k + \lambda_k d_{vk}) \quad (23)$$

$$x_{k+1} = x_k - \frac{1}{2} \lambda_k V A^T \overline{A} d_{vk} \quad (24)$$

$$x_{k+1} = x_k - \lambda_k \delta_{xk} \quad (25)$$

$$d_{p(k+1)} = A x_{k+1} - b \quad (26)$$

$$d_{p(k+1)} = d_{pk} - \frac{1}{2} \lambda_k A V A^T \overline{A} d_{vk} \quad (27)$$

$$d_{p(k+1)} = d_{pk} - \lambda_k \delta_{pk} \quad (28)$$

$$d_{v(k+1)} = \overline{A}^T d_{p(k+1)} \quad (29)$$

$$d_{v(k+1)} = d_{vk} - \tfrac{1}{2}\lambda_k \overline{A}^T A V A^T \overline{A} d_{vk} \quad (30)$$

$$d_{v(k+1)} = d_{vk} - \lambda_k \delta_{vk} \quad (31)$$

Embodiments of the disclosure comprise determining the optimal relaxation parameter based on minimizing the magnitude of the proton deviation vector $d_p$ (relationships (32)-(35) below) or the voxel deviation vector $d_v$ (relationships (36)-(39) below).

$$\frac{\partial}{\partial \lambda_k}(d_{p(k+1)} \cdot d_{p(k+1)}) = -2\delta_{pk}(d_{pk} - \lambda_k \delta_{pk}) \quad (32)$$

$$\frac{\partial}{\partial \lambda_k}(d_{p(k+1)} \cdot d_{p(k+1)}) = 2\lambda_k(\delta_{pk} \cdot \delta_{pk}) - 2(\delta_{pk} \cdot d_{pk}) \quad (33)$$

$$\frac{\partial}{\partial \lambda_k}(d_{p(k+1)} \cdot d_{p(k+1)}) = 0 \quad (34)$$

$$\lambda_k = \frac{\delta_{pk} \cdot d_{pk}}{\delta_{pk} \cdot \delta_{pk}} \quad (35)$$

$$\frac{\partial}{\partial \lambda_k}(d_{v(k+1)} \cdot d_{v(k+1)}) = -2\delta_{vk}(d_{vk} - \lambda_k \delta_{vk}) \quad (36)$$

$$\frac{\partial}{\partial \lambda_k}(d_{v(k+1)} \cdot d_{v(k+1)}) = 2\lambda_k(\delta_{vk} \cdot \delta_{vk}) - 2(\delta_{vk} \cdot d_{vk}) \quad (37)$$

$$\frac{\partial}{\partial \lambda_k}(d_{v(k+1)} \cdot d_{v(k+1)}) = 0 \quad (38)$$

$$\lambda_k = \frac{\delta_{vk} \cdot d_{vk}}{\delta_{vk} \cdot \delta_{vk}} \quad (39)$$

In step 1106, the system may determine a plurality of relationships for the voxel deviation vector $d_v$, proton deviation vector $d_p$, and RSP value x. Step 1106 may use a plurality of vectors, such as s vector, p vector, and v vector to represent these relationships. The relationships may be:

$$s_0 = x_0 \quad (40)$$

$$p_0 = d_{p0} \quad (41)$$

$$v_k = \overline{A}^T p_k \quad (42)$$

$$s_{k+1} = \tfrac{1}{2} V A^T \overline{A} v_k \quad (43)$$

$$p_{k+1} = A s_{k+1} \quad (44)$$

The RSP map update may involve a global optimization for several iterations, for example, that begins with the original RSP value: $x_o = x_x$ and simultaneously optimizes relationships (40) to (44) comprising the s, p, and v vectors.

For a given iteration n, the relationships may be expressed in relation to voxel deviation vector $d_v$, proton deviation vector $d_p$, and RSP value x, with coefficients $\kappa_i$ to be determined:

$$d_{pn} = p_0 + \sum_{i=1}^{n} \kappa_i p_i \quad (45)$$

$$d_{vn} = v_0 + \sum_{i=1}^{n} \kappa_i v_i \quad (46)$$

$$x_n = s_0 + \sum_{i=1}^{n} \kappa_i s_i \quad (47)$$

These expressions can be reformulated for purposes of determining the goodness of fit, in step 1108. In some embodiments, determining the goodness of fit comprises performing a chi-square minimization process (minimizing chi-square $\chi^2$).

$$d_{pn} = d_{p0} + \frac{1}{2}\sum_{i=1}^{n} \kappa_i A V A^T \overline{A} v_{i-1} \quad (48)$$

$$d_{pn} = A\left(x_0 + \frac{1}{2}\sum_{i=1}^{n} \kappa_i V A^T \overline{A} v_{i-1}\right) - b \quad (49)$$

Given the proton deviation vector ($d_{pn} = A x_n - b$):

$$x_n = x_0 + \frac{1}{2}\sum_{i=1}^{n} \kappa_i V A^T \overline{A} v_{i-1} \quad (50)$$

Chi-square $\chi^2$ after n iterations is:

$$\chi^2 = d_{pn} \cdot d_{pn} \quad (51)$$

$$\chi^2 = (\Sigma_{i=0}^n \kappa_i^n p_i) \cdot (\Sigma_{i=0}^n \kappa_i^n p_i) \quad (52)$$

$$\chi^2 = \Sigma_{i,j=0}^n \kappa_i^n \kappa_j^n p_i \cdot p_j \quad (53)$$

where $\kappa_0^n = 1$.

Chi-square $\chi^2$ can be minimized to determine the values of $\kappa_i^n$ (related to the proton deviation vector $d_p$, as shown in relationship (51)) corresponding to the solution closest to the optimum. Embodiments of the disclosure comprise determining the updated RSP map values $x_n$ directly from the $\kappa_i^n$ and the s vectors (relationship (47) above). In some embodiments, to the method may exclude determining individual relaxation parameters.

One non-limiting example for minimizing chi-square $\chi^2$ comprises setting its gradient to 0, resulting in:

$$d\chi^2 / d\kappa_i^n = 2\Sigma_{j=0}^n \kappa_j^n p_i \cdot p_j = 0 \quad (54)$$

$$p_i \cdot p_0 + \Sigma_{j=1}^n \kappa_j^n p_i \cdot p_j = 0 \quad (55)$$

The relationship may be reduced to solving for $k^n$, when $P^n$ is an array of $p_i \cdot p_j$, $k^n$ is a vector of $\kappa_j^n$, and $p^n$ as the vector of $-p_i \cdot p_0$.

$$P^n k^n = p^n \quad (56)$$

As another non-limiting example, chi-square $\chi^2$ can be expressed in relation to the voxel deviation vector (for a given iteration n) $d_{vn}$, leading to:

$$\chi^2 = d_{vn} \cdot d_{vn} \quad (57)$$

$$V^n k^n = v^n \quad (58)$$

In step 1110, the system may evaluate whether a stopping criteria has been met. If the stopping criteria has been met, the RSP update method is complete (step 1112). If not, the system may repeat one or more steps of method 1100 until the stopping criteria has been met. The stopping criteria may be such that the updated RSP image becomes quantifiably close to optimal and can be applied to any object being imaged.

The above methods for optimizing the chi-square $\chi^2$ of the solution after a number of iterations n can be used to evaluate whether further iterations are needed, or whether the current solution is close enough to the optimal solution. In some embodiments, additional iterations of the s, p, and v vectors may be produced, while the optimal coefficients may be determined and/or the quality of the fit may be evaluated in parallel. Additionally or alternatively, the step size for each iteration may be individually determined or adjusted. In some embodiments, the step sizes of a plurality of iterations may be optimized in parallel.

Embodiments of the disclosure may comprise determining whether the stopping criteria has been met based on the determined goodness of fit (chi-square $\chi^2$ per degree of freedom) of step 1108. An average deviation per proton may be determined based on chi-square $\chi^2$:

$$\sigma_P = (\chi^2/N_p)^{1/2} \qquad (59)$$

where $N_p$ is the total number of protons and $N_v$ is the total number of voxels. Further, an estimated average voxel precision may be determined as:

$$\sigma_V = (\sigma_{Pk}/N_{pv})^{1/2} \qquad (60)$$

where $N_{pv}$ is the average number of protons touching a voxel.

In some embodiments, if a region of the image has uniform RSP, the estimated average voxel precision $\sigma_V$ can be determined from the image in that region. In some embodiments, the stopping criteria may be based on the root-mean-square (r.m.s.) of a given iteration, such as the r.m.s. of the deviation being less than a pre-determined precision value. For example, if the r.m.s. of proton deviation vector $d_v$ is less than a factor of the estimated average voxel precision (r.m.s. $d_v < f\sigma_V$), the noise from the proton measurement uncertainties is greater than the remaining distance to the optimal solution, and method 1100 may end. In some embodiments, the factor f may be between 0.5-1. In some embodiments, the factor f may depend on whether the protons are from a single or reduced number of directions (compared to an entire scan). For example, the factor f may be greater than 1, and increased by an estimate of the average correlation between voxels.

Additionally or alternatively, the stopping criteria may be based on whether the average deviation per proton $\sigma_p$ is less than the WEPL precision per proton or a factor of it ($\sigma_p < c$, where c is proportional to the WEPL). As another example, the stopping criteria may comprise the maximum of the magnitude of the proton deviation vector $d_v$ being less than the WEPL precision per proton (max $|d_v| < c_v$) or the maximum of the magnitude of the sum of the proton deviation vector $d_v$ over a certain volume (voxel volume) being less than the WEPL precision per proton (max |sum of $d_v$ over nxnxn voxel volume|$<c_v$). In some embodiments, the r.m.s. of proton deviation vector $d_v$ and/or estimated average voxel precision $\sigma_v$ may be calculated from only voxels in a region of interest.

Example Estimation of Remaining Range Uncertainties

After the image registration and RSP update steps (steps 902 and 904, respectively) are performed, changes to the treatment plan (differences between the updated RSP map and original RSP map) may be large, and a decision on whether to adapt the plan or stop the treatment to acquire a new planning CT and new treatment plan may depend on an evaluation of the remaining range uncertainties (step 912). Since the true values are not known, the evaluation may be difficult.

One method is to temporarily modify the original RSP map, obtain a new solution using the proton data, and compare the new solution to the one using the original RSP map and the same proton data. For example, the RSP of the voxels along the treatment direction to a tumor could be scaled by a certain percentage, or a subset of these voxels could be scaled. The change in the range to the tumor in the original and new solutions can be compared with each other. The change may correspond to a pre-determined difference used in step 908 and/or 912 to establish the degree to which range uncertainties can be corrected by the proton data. This change in range may indicate the need for additional proton data, or indicate that the remaining range uncertainty is too large.

Example Images

Embodiments comprise using the methods and systems disclosed herein for pCT image reconstruction to account for differences between the original image and an updated image (e.g., taken right before treatment). For example, the original image may have been taken when sinuses of a patient were filled, but the updated image may be taken when sinuses were empty. As another example, the methods may be used to correct for uncertain values, such as RSP values in the original image.

Figure 12:
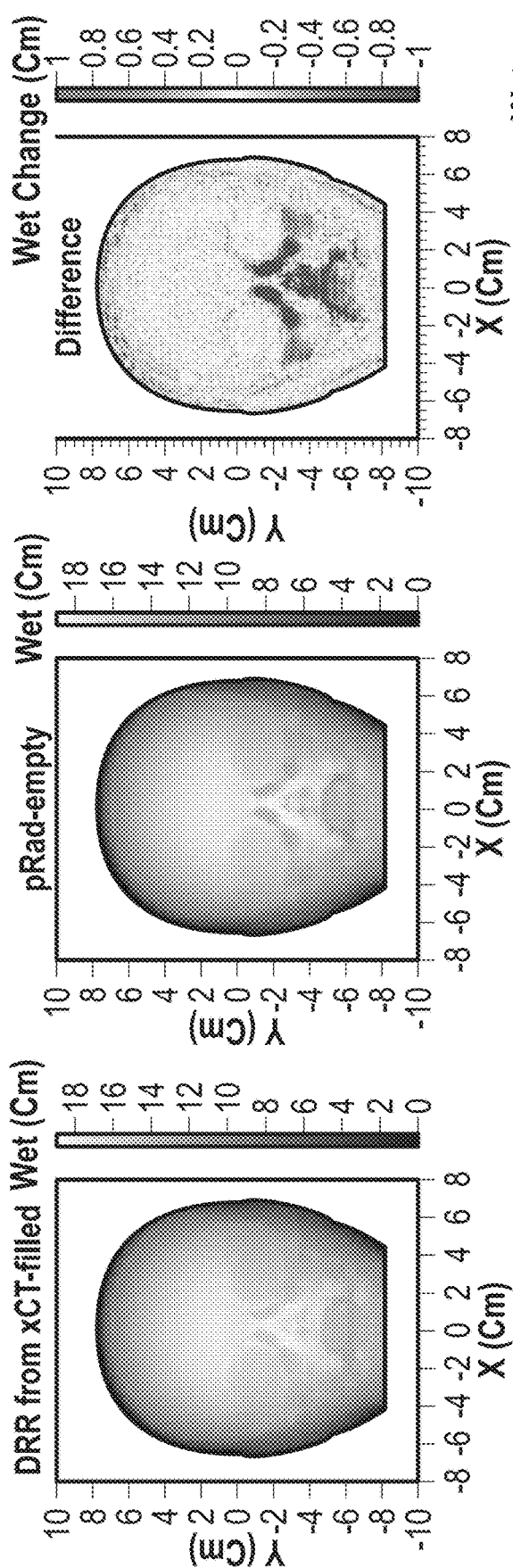
FIG. 12 illustrates example simulated data for a pediatric head phantom using the disclosed methods, according to some embodiments.
Figure 12:
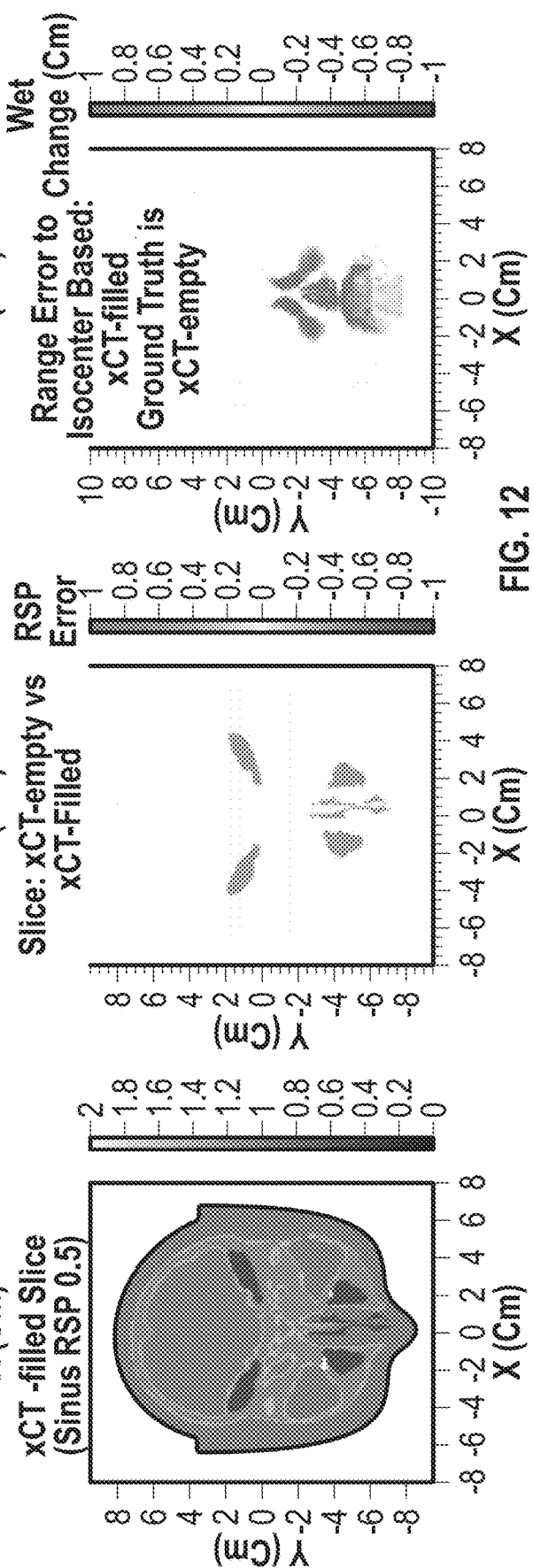

FIG. 12 illustrates example simulated data for a pediatric head phantom using the disclosed methods. The simulations were done with sinuses filled and sinuses empty. A treatment based on an image with sinuses filled may have large range errors if the sinuses are empty at the time of treatment. The top left image shows a digitally reconstructed radiograph (DRR) from a simulation with the sinuses filled. The top middle image shows a pRad simulation with the sinuses empty. The top right illustrates the difference between the top left image and the top middle image. The bottom left image illustrates an axial slice with sinuses filled. The bottom middle image illustrates the difference between the axial slice with sinuses filled image (bottom left) and a slice with sinuses empty. The bottom right image illustrates the range error used CT with sinuses filled if the sinuses are empty.

Figure 13:
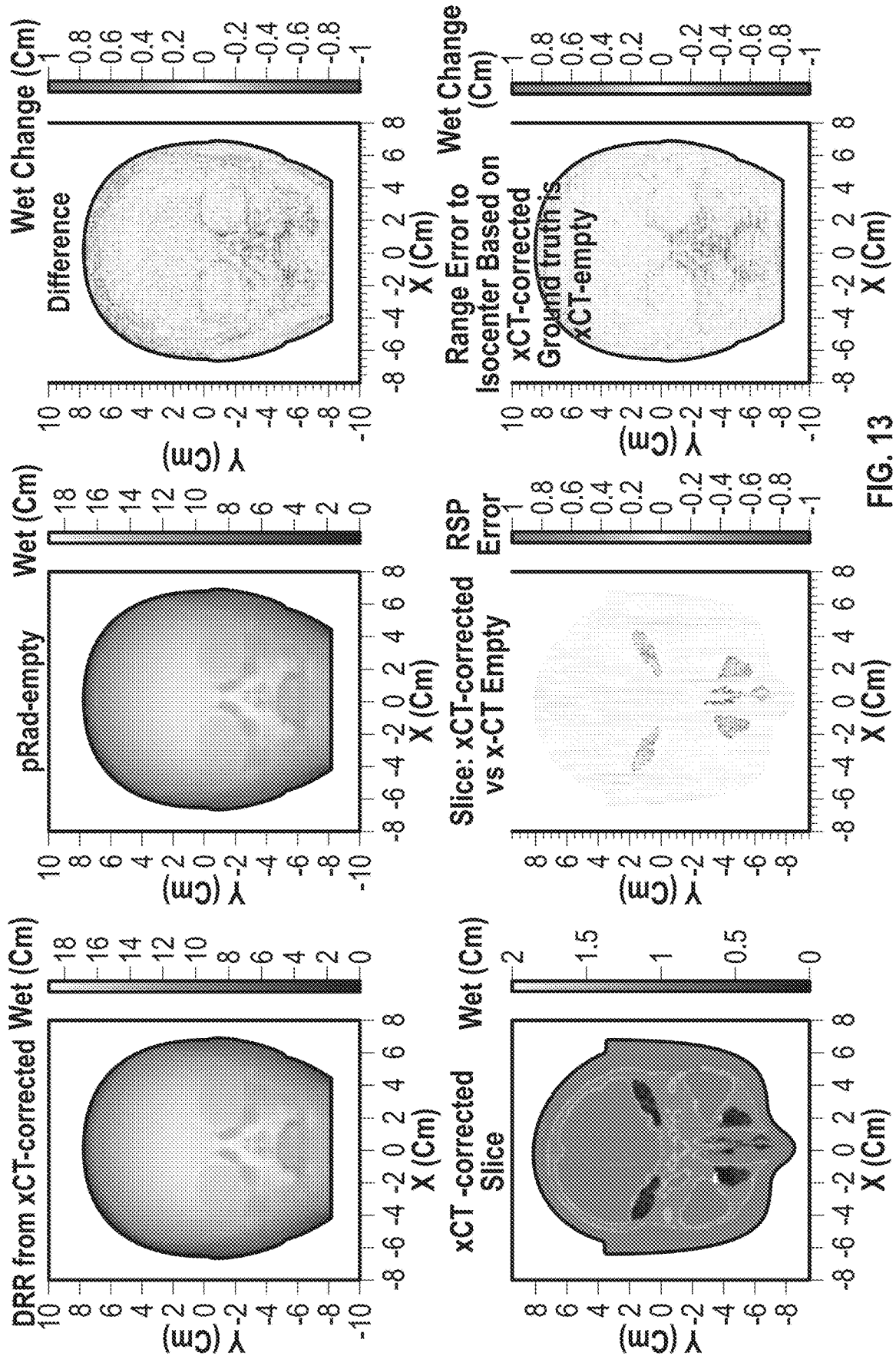
FIG. 13 illustrates an example result of correcting a CT image with the sinuses filled using the protons from a single pRad with the sinuses empty, according to some embodiments.

FIG. 13 illustrates an example result of correcting a CT image with the sinuses filled using the protons from a single pRad with the sinuses empty. Since the sinus voxels can have uncertain RSP values, the uncertainties for the sinus voxels in the example were assigned an uncertainty 10 times that of the other voxels. In this way, the protons from a single pRad can greatly reduce the range uncertainties. The figure illustrates a DRR from the corrected RSP map (top left), pRad with sinuses empty (top middle), and the difference between corrected RSP map and pRad with sinuses empty in the top right image. The bottom left image illustrates an axial slice from the corrected CT, the bottom middle image illustrates the difference with the CT with sinuses empty, and the bottom right image illustrates the corresponding range errors using corrected CT.

Figure 14:
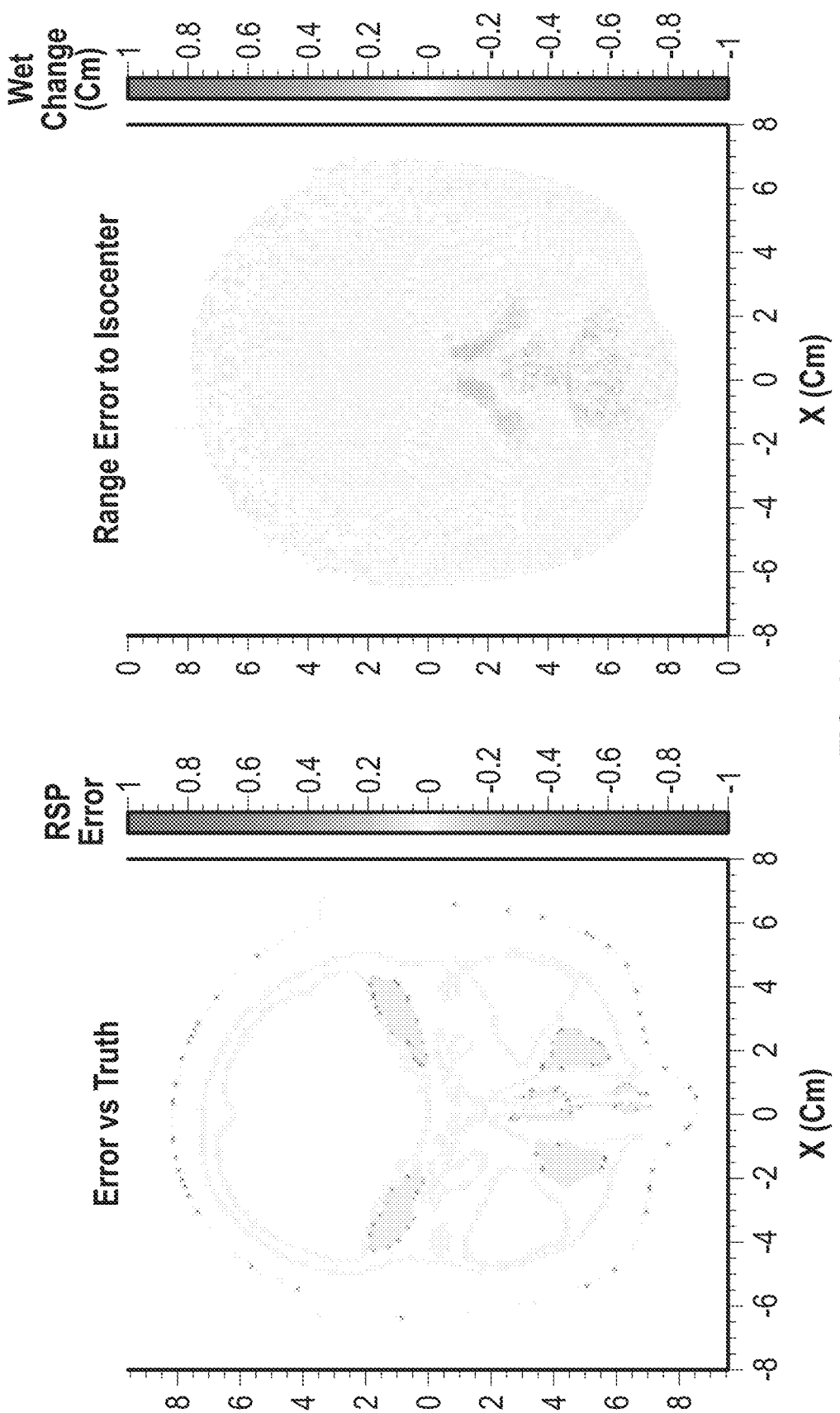
FIG. 14 illustrates an example method of reducing range uncertainties, according to some embodiments.

FIG. 14 shows that the range uncertainties can be further reduced, in some instances, with the assumption that all the voxels in the sinuses have correlated uncertainties. This may not be the case for all instances, such as when sinuses are partially filled, but apply when tissues have a poor Hounsfield unit to proton RSP conversion. The figure provides example images that are based on correcting the CT with sinuses filled using protons from the pRad with sinuses empty. The sinus voxels were assigned correlated uncertainties. The left image illustrates the difference with the CT with sinuses empty. The right image illustrates range errors using corrected CT.

Figure 15:
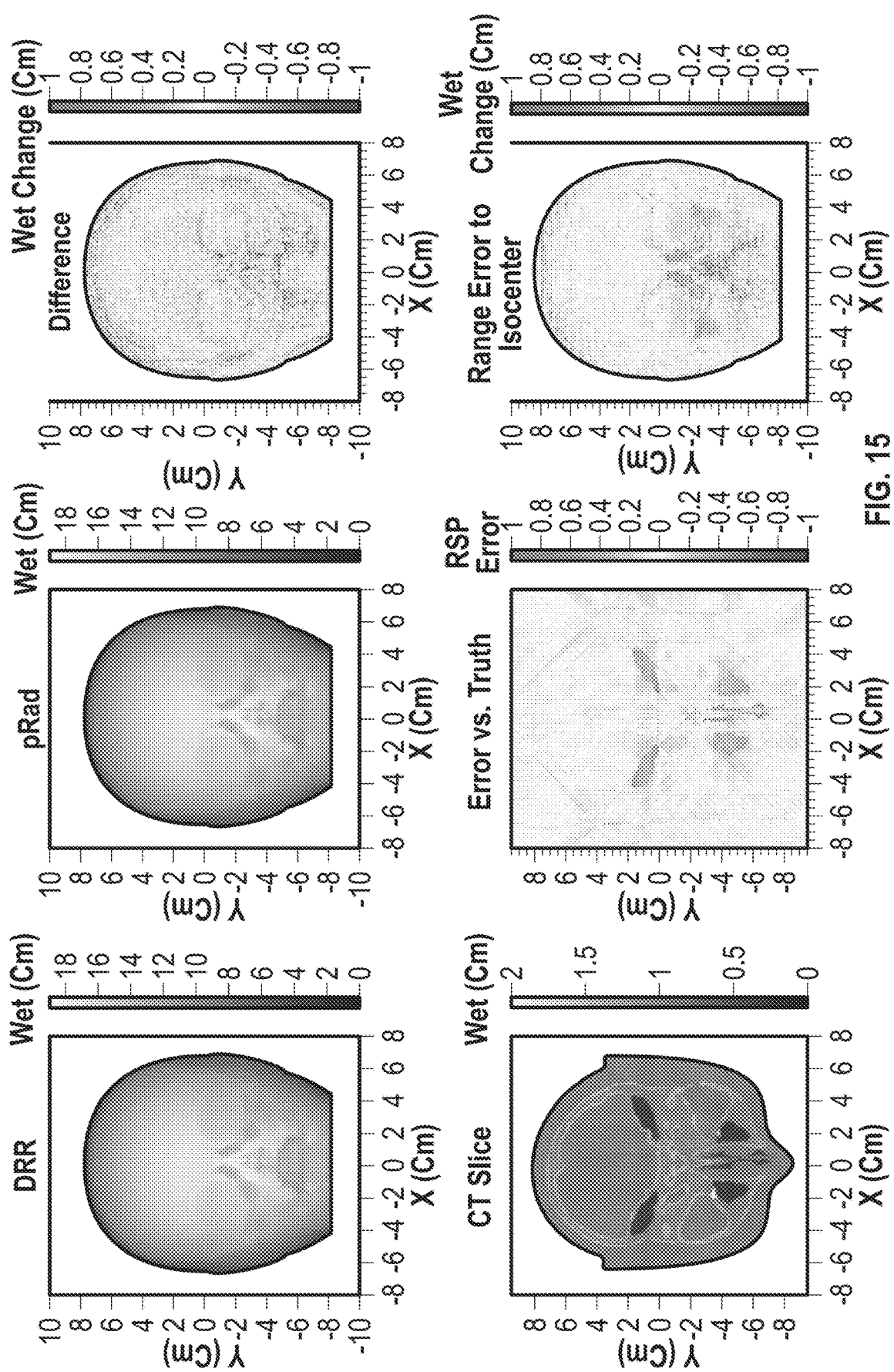
FIG. 15 illustrates an example method of using protons from multiple directions, according to some embodiments.

FIG. 15 shows that using protons from multiple directions can also reduce range uncertainties, even if the sinus voxels are not assumed to have larger uncertainties. A CT with sinuses filled may be corrected using protons from four pRads with sinuses empty, for example. As shown in the image, a DRR from the corrected RSP map (top left) and pRad with sinuses empty (top middle). The difference between the two images (correct RSP map and pRad) is shown in the top right image. The bottom images (left to right) illustrate an axial slice from the corrected CT, difference with the CT with sinuses empty, and range errors using corrected CT.

Exemplary Methods for Memory Use

Memory resources can be a bottleneck in the implementation of the methods described according to the examples of the disclosure. In some examples, while the proton-voxel matrix (e.g., an A matrix comprising one row for each proton and one column for each voxel) may be large, it may be sparse as each proton may touch only a small number of voxels. The sparsity of the A matrix may be used to store data in a compact manner. For example, the entries in the A matrix may be stored as lists of voxels with chord lengths for each proton, or as lists of protons with chord lengths for each voxel. In some instances, the lists include only non-zero chord-lengths, but still require a large amount of storage. Data sets for adaptive planning in many cases may be much smaller than those for pCT, allowing more options.

In some examples, entries in a matrix (e.g., A matrix) are stored as lists of voxels with chord lengths for each proton, where the geometry to store this information with much less memory can be taken advantage of. For example, each proton may have a list of line segments that can be used to recreate the chord lengths when needed. Each line segment should be short enough that a straight line approximates the proton trajectory to appropriate accuracy within the segment. In some examples, each proton can have a list of chord lengths, each typically stored in one byte, and a second list of base-6 numbers, stored in 4-byte integers with 12 base-6 numbers included in each 4-byte integer. Starting from a given voxel, the first base-6 number specifies the voxel face that the proton exits, and thus the identity of the next voxel, and subsequent base-6 numbers continue the chain from there. Thus, the chord lengths can be associated with the correct voxel.

Figure 16:
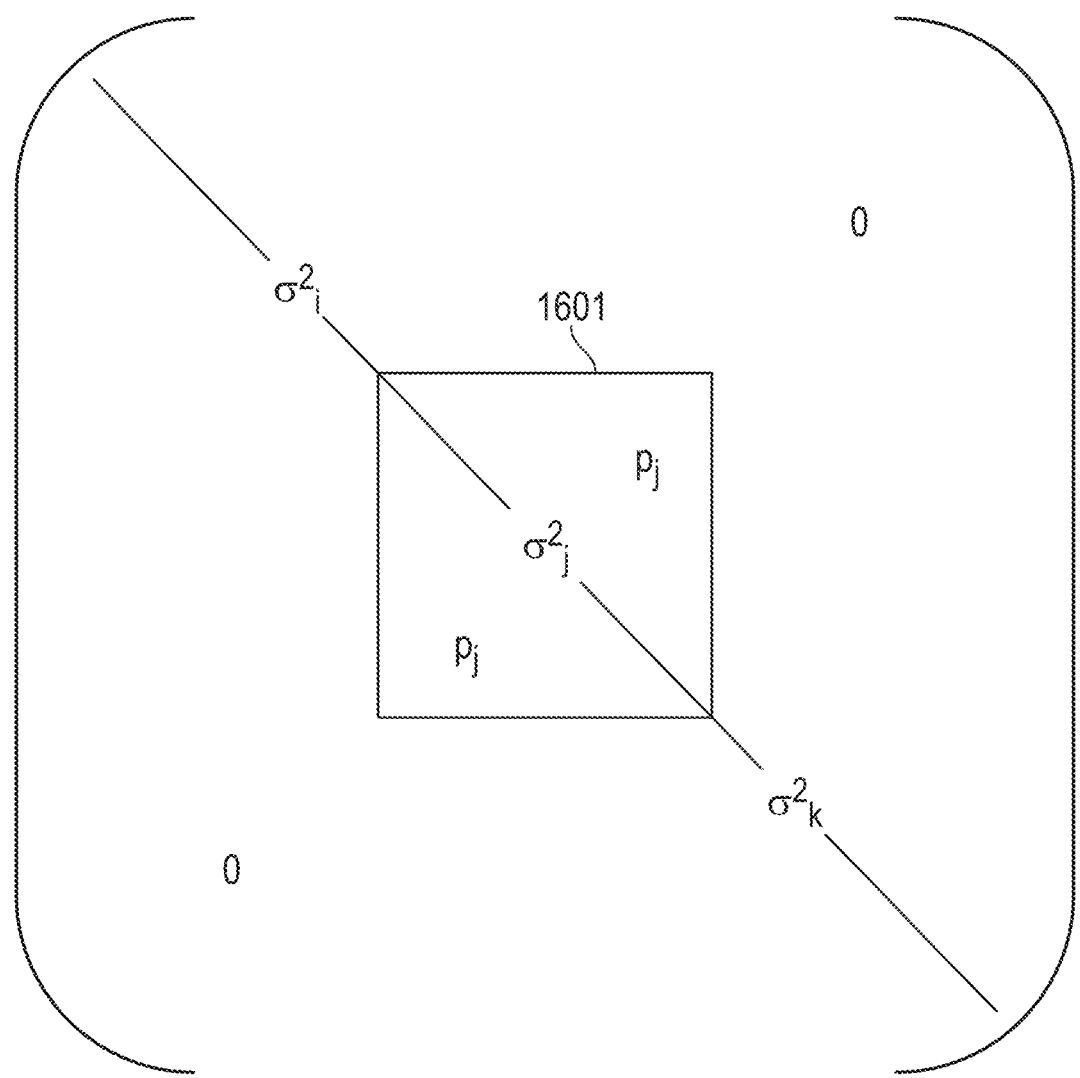
FIG. 16 illustrates an example method of storing a covariance matrix, according to some embodiments.

The covariance matrix V (discussed above) may require a large amount of storage and computational power for multiplications. Embodiments of the disclosure comprise storing the covariance matrix V compactly, as illustrated in FIG. 16. In some embodiments, all the voxels in a region is assigned the same variance and correlation coefficients, reducing the amount of storage required. For example, entries for three regions are shown: i, j, k with the voxels ordered such that the entries for each region appear adjacent in the matrix. Each voxel can be assigned an individual variance, which appears on the diagonal, and in this example, all the voxels in a region have the same variance, and voxel pairs within the same region 1601 may be assigned the same non-zero covariance. Additionally, the multiplications with the covariance matrix V can be done very efficiently in this case.

Exemplary Methods for Parallel Processing

In some instances, processing may be performed in blocks with arbitrarily small numbers of protons, where the results are generated as if the calculations were executed in a single block. Bottlenecks may involve memory resources, CPU resources, GPU resources, and data transfer capacity. Choice of strategy will depend on the resources of a particular computing system, and implementation will rely on appropriate design of data structures and software architectures.

In some examples, the computationally costly part of each full iteration may involve a sequence of two matrix-vector multiplications for either $\overline{A}^T(Ad_{vk})$ or $\overline{A}^T(Av_k)$, as described above, saving intermediate vectors. In a matrix-vector multiplication, each row of the matrix multiplies the vector independently. In some embodiments, all the row-vector multiplications may be performed in parallel using, e.g., GPUs. These multiplications may be performed using the strategies discussed below.

Exemplary Row-Column DV (RCDV)

Figure 17:
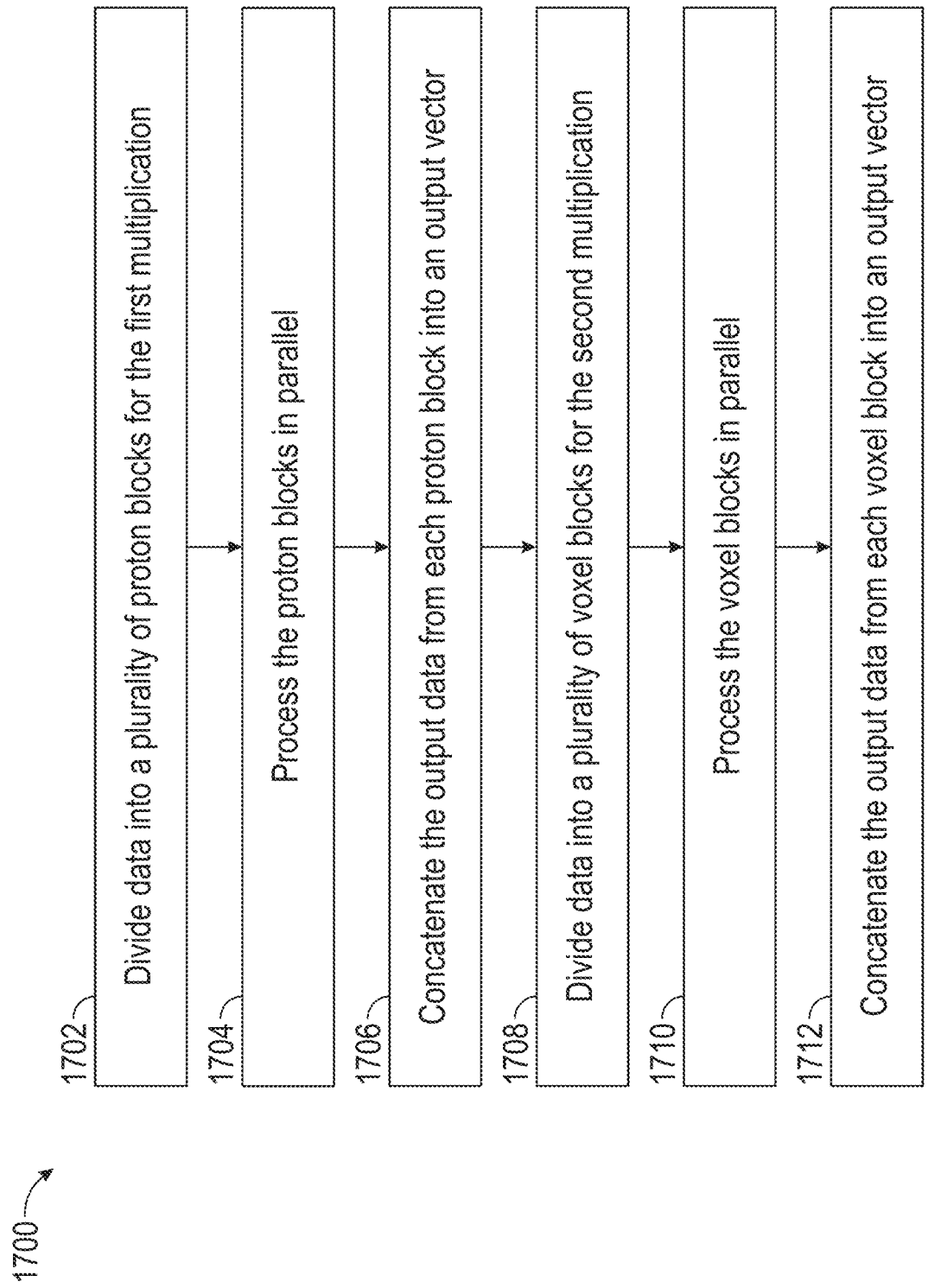
FIG. 17 illustrates an exemplary method for parallel processing, according to some embodiments.

FIG. 17 illustrates an exemplary method for parallel processing, according to some embodiments. In some examples, the most straightforward strategy may be performed in a plurality of steps as shown in method 1700. In step 1702, the data may be divided into blocks of protons for a first multiplication $Av_k$.

In step 1704, the proton blocks may be processed in parallel, where the blocks may be as small as a single proton. The parallel processing may equally account for a plurality (e.g., all) protons for each iteration. This unlike sequential processing methods where the last proton has a disproportional impact. In step 1706, the outputs from each of the blocks may be concatenated to be assembled into an output vector. In step 1708, the data may be divided into blocks of voxels for the second multiplication $\overline{A}^T(Av_k)$. In step 1710, the voxel blocks may be processed in parallel, where the blocks may be as small as a single voxel. In step 1712, the outputs from each of the blocks may be concatenated to assemble an output vector.

In some examples, the blocks may be processed in worker processes, outputs may be assembled in a foreman process, and results evaluated in an executive process. Blocks may further be divided into sub-blocks, and a hierarchical system of blocks may help route calculations to multiple GPUs.

In some embodiments, the method 1700 may use lists of voxels with chord lengths for each proton, as well as lists of protons with chord lengths for each voxel.

Exemplary Coordinated Blocks DV (CBDV)

Figure 18:
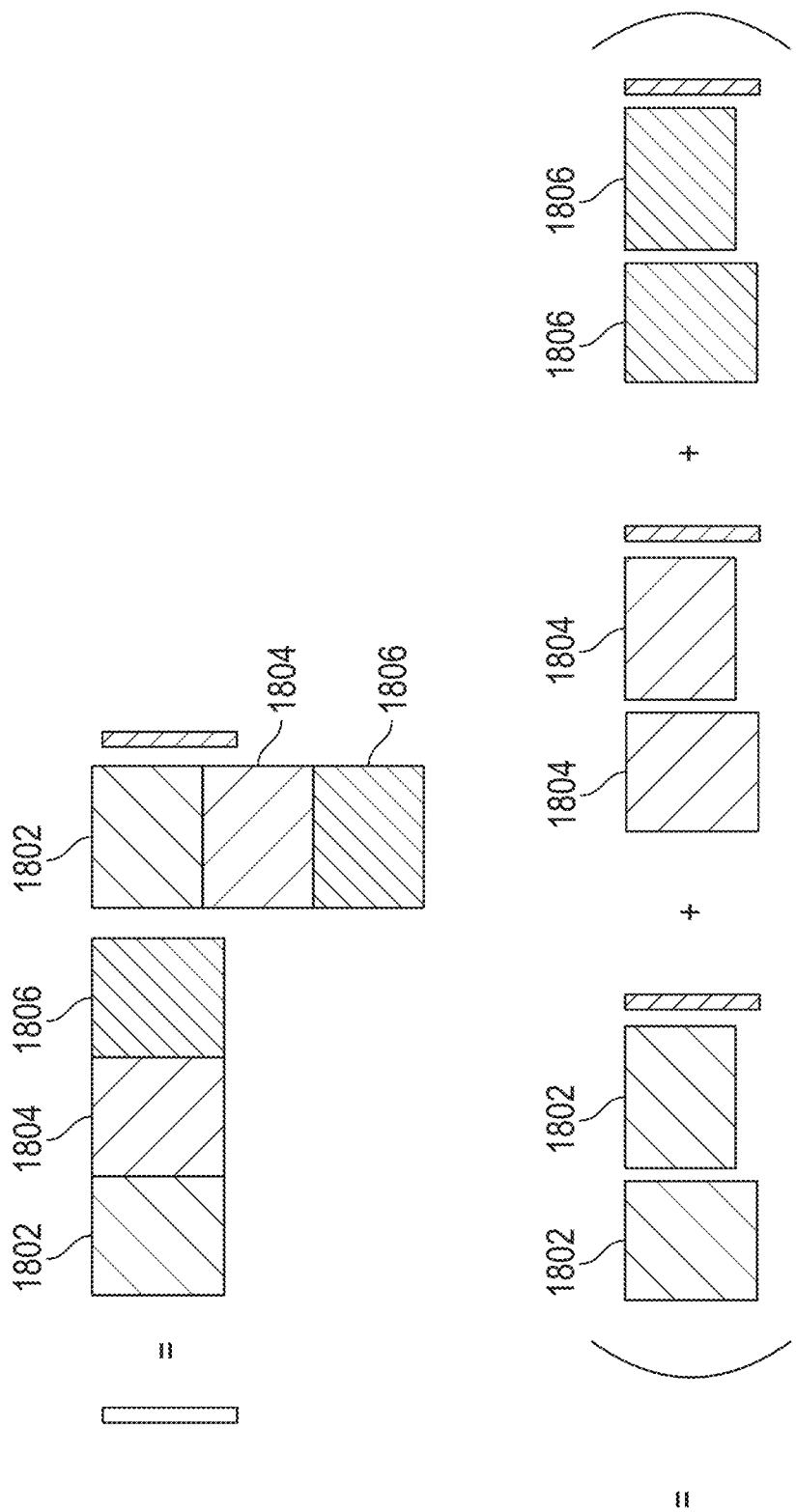
FIG. 18 illustrates data for different blocks of protons 1802, 1804, and 1806 in the form of matrices, according to some embodiments.

In some embodiments, the sequence of multiplications may be carried out independently in different blocks of protons, each with a worker process, and with each block t producing output vectors $[\overline{A}v_k]_t$ and $[A^T(\overline{A}v_k)]_t$. FIG. 18 illustrates data for different blocks of protons 1802, 1804, and 1806 in the form of matrices. In some embodiments, each block 1802, 1804, and 1806 may include chord length data for different entries in the proton-voxel matrix (e.g., A matrix). As discussed above, in the A matrix, a row can include data for one proton, and an entry can include more than one row. For $A^T$, the data for a proton is in a column. The blocks 1802, 1804, and 1806 can represent matrices, with matrix-matrix (or matrix-vector) multiplications multiplying rows from the matrix on the left with a column from the matrix (or vector) on the right. As with RCDV, the foreman process can concatenate the $[\overline{A}v_k]_t$ vectors into the complete $\overline{A}v_k$ vector. Obtaining the complete $\overline{A}^T(Av_k)$ is a sum over the blocks:

$$A^T(\overline{A}v_k) = \Sigma_t [A^T(\overline{A}v_k)]_t \quad (61)$$

In some embodiments, the complete vectors are identical to what would be obtained with a single block and are the input to the next iteration.

In some examples, a hierarchy of blocks may be employed. For example, if the system includes 10 GPUs, the data can be divided into one block for each GPU. Within each block, each proton may be processed as a separate sub-block utilizing the parallel processing power of the GPUs, carefully managing the summation of the output vectors from each proton.

Processing each proton independently (blocks of size one proton) may enable major savings in the use of memory. First, there is no need for a list of protons with chord lengths for each voxel. All the needed information is with the list of voxels with chord lengths for each proton, and the output vector needs only the voxels from that proton. Second, the geometry to store this information with much less memory strategies, such as those described above, can be taken advantage of.

Exemplary Independent Blocks DV (IBDV)

In some examples, a method to optimize data processing may be implemented without developing a parallel processing architecture such as foreman processes, and may provide a convenient method for rapid studies. Protons may be divided into N well-randomized and equal-sized blocks t (the method may be extended to different sized blocks, where the assignment of a proton to a block is random). In some embodiments, each block includes enough protons to find a solution vector (more protons than voxels). The system and process for handling a single block of protons may then be run N times in parallel, to produce a solution for each block where the solution may be close to the minimum chi-square $\chi^2$ for that block.

In this case, the following may hold within the statistical variability of the data for each block, where the normalization of $\overline{A}^t$ is done using only the protons in that block:

$$\overline{A}^T A \approx \overline{A}^{tT} A^t \quad (62)$$

$\overline{A}^T A$ is a square matrix with dimension equal to the number of voxels, where each entry is a ratio. The numerator and denominator both, on average, scale linearly with the number of protons, and each entry is, on average, independent of the number of protons. At minimum chi-square $\chi^2$, the following relationships are determined:

$$\overline{A}^T A x = \overline{A}^T b \quad (63)$$

$$\overline{A}^T A x = V^{-1} A^T b \quad (64)$$

$$\overline{A}^T A x = \Sigma_t V^{-1} A^{tT} b^t \quad (65)$$

$$\overline{A}^T A x = \Sigma_t V^{-1} V_t \overline{A}^{tT} b^t \quad (66)$$

$$\overline{A}^T A x = \Sigma_t V^{-1} V_t \overline{A}^{tT} A^t x^t \quad (67)$$

$$\overline{A}^T A x \approx 1/N \Sigma_t \overline{A}^{tT} A^t x^t \quad (68)$$

$$\overline{A}^T A x \approx 1/N \overline{A}^T A \Sigma_t x^t \quad (69)$$

The average of the solution vectors from the blocks may become:

$$x \approx 1/N \Sigma_t x^t \quad (70)$$

Exemplary Computer

Figure 19:
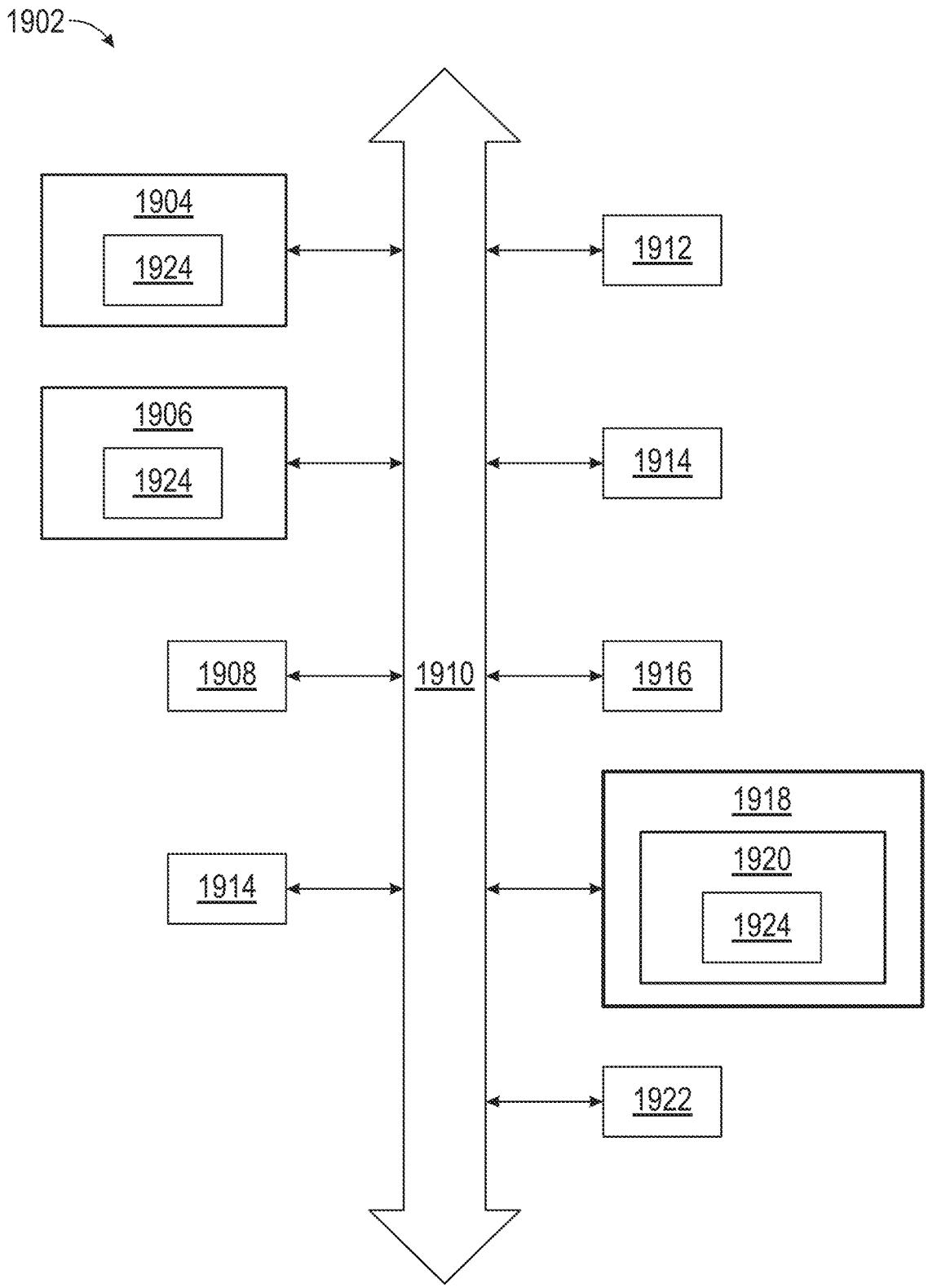
FIG. 19 illustrates a block diagram of an exemplary server computer, according to some embodiments.

FIG. 19 illustrates a block diagram of an exemplary server computer 1902, according to embodiments of the disclosure. The server computer 1902 may be a machine such as a computer, within which a set of instructions, causes the machine to perform any one of the methodologies discussed herein, may be executed, according to embodiments of the disclosure. In some embodiments, the machine can operate as a standalone device or may be connected (e.g., networked) to other machines. In a networked configuration, the machine may operate in the capacity of a server or a client machine in a server-client network environment, or as a peer machine in a peer-to-peer (or distributed) network environment. The machine can be a personal computer (PC), a tablet PC, a set-top box (STB), a personal digital assistant (PDA), a cellular telephone, a web appliance, a network router, a switch or bridge, or any machine capable of executing a set of instructions (sequential or otherwise) that specify actions to be taken by that machine. A mobile device such as a PDA or a cellular phone may also include an antenna, a chip for sending and receiving radio frequency transmissions and communicating over cellular phone WAP and SMS networks, and a built-in keyboard. Further, while only a single machine is illustrated, the term "machine" shall also be taken to include any collection of machines that individually or jointly execute a set (or multiple sets) of instructions to perform any one of the methodologies discussed herein.

The exemplary computer 1902 includes a processor 1904 (e.g., a central processing unit (CPU), a graphics processing unit (GPU), or both), a main memory 1906 (e.g., read-only memory (ROM), flash memory, dynamic random access memory (DRAM) such as synchronous DRAM (SDRAM) or Rambus DRAM (RDRAM), etc.), and a static memory 1908 (e.g., flash memory, static random access memory (SRAM), etc.), which can communicate with each other via a bus 1910.

The computer 1902 may further include a video display 1912 (e.g., a liquid crystal display (LCD) or a cathode ray tube (CRT)). The computer 1902 also includes an alphanumeric input device 1914 (e.g., a keyboard), a cursor control device 1916 (e.g., a mouse), a disk drive unit 1918, a signal generation device 1920 (e.g., a speaker), and a network interface device 1922.

The drive unit 1918 includes a machine-readable medium 1920 on which is stored one or more sets of instructions 1924 (e.g., software) embodying any one or more of the methodologies or functions described herein. The software may also reside, completely or at least partially, within the main memory 1906 and/or within the processor 1904 during execution thereof by the computer 1902, the main memory 1906 and the processor 1904 also constituting machine-readable media. The software may further be transmitted or received over a network 1904 via the network interface device 1922.

While the machine-readable medium 1920 is shown in an exemplary embodiment to be a single medium, the term "machine-readable medium" should be taken to include a single medium or multiple media (e.g., a centralized or distributed database and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A method comprising:
performing image registration to account for differences between an original image and an updated image;
updating an original relative stopping power (RSP) map corresponding to the original image using individual proton measurement data, wherein the individual proton measurement data are associated with the updated image;
comparing the updated RSP map to the original RSP map, wherein the original image corresponds to the original RSP map; and quantifying changes between the updated map and the original RSP map.

2. The method of claim 1, wherein the performing image registration and the updating the original RSP map steps are performed without use of a reconstructed proton radiography (pRad) image.

3. The method of claim 1, wherein the performing image registration comprises iteratively determining a deformation field based on a distance of a voxel deviation vector relative to a deformed template image prediction.

4. The method of claim 3, further comprising:
determining the voxel deviation vector based on the individual proton measurement data deformed template image.

5. The method of claim 1, wherein the performing image registration comprises matching the original RSP map using individual proton trajectories and water equivalent path length (WEPL) measurements.

6. The method of claim 1, wherein the updating the original RSP map comprises matching the individual proton measurement data to values of the original RSP map.

7. The method of claim 1, wherein the updating the original RSP map comprises assigning different uncertainties to different regions of the updated image.

8. The method of claim 1, wherein the updating the original RSP map comprises optimizing a deviation of the individual proton measurement data from values of the original RSP map.

9. The method of claim 8, wherein the deviation comprises a voxel deviation or a proton deviation.

10. The method of claim 8, wherein the optimizing a deviation comprises:
searching for minimums and maximums in the deviation;
determining the relaxation parameter based on a magnitude of the deviation;
determining a plurality of relationships between the deviation and the updated RSP map;
determining a goodness of fit of the plurality of relationships; and
repeating the searching and determining steps until a stopping criteria has been met, wherein the stopping criteria is associated with the determined goodness of fit.

11. The method of claim 10, wherein the searching for minimums and maximums in the deviation comprises, for each iteration, determining an updated RSP value and updating Lagrange multipliers.

12. The method of claim 10, wherein the determining the goodness of fit comprises performing a chi-square minimization process.

13. The method of claim 10, wherein the stopping criteria comprises a root-mean-square of the deviation being less than a pre-determined precision value.

14. The method of claim 1, further comprising:
assigning uncertainties or correlations to voxels in the updated RSP map using a covariance matrix.

15. The method of claim 14, wherein the voxels in a region are assigned the same uncertainties or correlations.

16. The method of claim 1, further comprising:
acquiring additional proton data in accordance with a difference between the updated RSP map and the original RSP map being greater than a pre-determined difference.

17. The method of claim 1, further comprising:
determining or adapting a plan based on the updated RSP map.

18. The method of claim 1, wherein positions, angles, or both, of the original image are different than positions, angles, or both, respectively, of the updated image.

19. A system comprising:
a source for generating a pencil beam of protons;
a scanning element for steering the pencil beam of protons;
a plurality of tracking detectors for generating photons, the photons corresponding to the pencil beam of protons interacting with an object;
a residual range detector; and
a computing system for receiving signals from the plurality of tracking detectors and the residual range detector, the computing system configured to:
perform image registration to account for differences between an original image and an updated image;
update an original RSP map corresponding to the original image using individual proton measurement data, wherein the individual proton measurement data are associated with the updated image;
compare the updated RSP map to the original RSP map, wherein the original image corresponds to the original RSP map; and
quantify changes between the updated map and the original RSP map.

20. The system of claim 19, wherein the computing system performs the image registration and the update of the original RSP map steps without use of a reconstructed proton radiography (pRad) image.

* * * * *